(12) United States Patent
Nakazawa et al.

(10) Patent No.: US 10,336,686 B2
(45) Date of Patent: Jul. 2, 2019

(54) FLUORINE ATOM-CONTAINING COMPOUND AND USE THEREOF

(71) Applicant: NISSAN CHEMICAL INDUSTRIES, LTD., Tokyo (JP)

(72) Inventors: Taichi Nakazawa, Funabashi (JP); Toshiyuki Endo, Funabashi (JP)

(73) Assignee: NISSAN CHEMICAL INDUSTRIES, LTD., Tokyo (JP)

(*) Notice: Subject to any disclaimer, the term of this patent is extended or adjusted under 35 U.S.C. 154(b) by 0 days.

(21) Appl. No.: 16/070,111

(22) PCT Filed: Jan. 11, 2017

(86) PCT No.: PCT/JP2017/000545
§ 371 (c)(1),
(2) Date: Jul. 13, 2018

(87) PCT Pub. No.: WO2017/122649
PCT Pub. Date: Jul. 20, 2017

(65) Prior Publication Data
US 2019/0031600 A1   Jan. 31, 2019

(30) Foreign Application Priority Data
Jan. 14, 2016 (JP) .............................. 2016-005375

(51) Int. Cl.
| | | |
|---|---|---|
| *C09D 7/40* | (2018.01) | |
| *C09K 11/06* | (2006.01) | |
| *H01L 51/00* | (2006.01) | |
| *H01L 51/50* | (2006.01) | |
| *C07C 209/10* | (2006.01) | |
| *C07C 209/18* | (2006.01) | |
| *C07C 211/54* | (2006.01) | |
| *C07C 231/02* | (2006.01) | |
| *C07C 233/80* | (2006.01) | |
| *C07C 273/18* | (2006.01) | |
| *C07C 275/40* | (2006.01) | |
| *C07C 303/34* | (2006.01) | |
| *C07C 311/21* | (2006.01) | |
| *C07C 327/48* | (2006.01) | |
| *C07C 335/20* | (2006.01) | |
| *C07D 209/86* | (2006.01) | |
| *C09D 201/00* | (2006.01) | |

(52) U.S. Cl.
CPC .......... *C07C 233/80* (2013.01); *C07C 209/10* (2013.01); *C07C 209/18* (2013.01); *C07C 211/54* (2013.01); *C07C 231/02* (2013.01); *C07C 273/1854* (2013.01); *C07C 275/40* (2013.01); *C07C 303/34* (2013.01); *C07C 311/21* (2013.01); *C07C 327/48* (2013.01); *C07C 335/20* (2013.01); *C07D 209/86* (2013.01); *C09D 7/40* (2018.01); *C09D 201/00* (2013.01); *C09K 11/06* (2013.01); *H01L 51/0055* (2013.01); *H01L 51/0056* (2013.01); *H01L 51/50* (2013.01); *H01L 51/506* (2013.01); *H01L 51/5012* (2013.01); *C07C 2603/18* (2017.05)

(58) Field of Classification Search
None
See application file for complete search history.

(56) References Cited

U.S. PATENT DOCUMENTS

| | | |
|---|---|---|
| 2008/0029742 A1 | 2/2008 | Yoshimoto et al. |
| 2010/0159279 A1 | 6/2010 | Kato et al. |
| 2010/0230639 A1 | 9/2010 | Yamada et al. |
| 2017/0062729 A1 | 3/2017 | Cha et al. |
| 2018/0163061 A1* | 6/2018 | Nakazawa .............. C07B 43/06 |

FOREIGN PATENT DOCUMENTS

| | | | |
|---|---|---|---|
| CN | 102408342 | * | 4/2012 |
| JP | 2007-153776 A | | 6/2007 |
| JP | 2008-27646 A | | 2/2008 |
| KR | 10-2014-0078096 A | | 6/2014 |
| KR | 10-2014-0128878 A | | 11/2014 |
| WO | WO 2006/025342 A1 | | 3/2006 |
| WO | WO 2008/032616 A1 | | 3/2008 |
| WO | WO 2008/129947 A1 | | 10/2008 |
| WO | WO 2010/058777 A1 | | 5/2010 |
| WO | WO 2015/041416 A1 | | 3/2015 |
| WO | WO 2015/174682 A1 | | 11/2015 |

OTHER PUBLICATIONS

Liu ("Deep-blue luminescent compound that emits efficiently both in solution and solid state with considerable blue-shift upon aggregation" J. Mater. Chem. C. 2014, 2, p. 1068-1075) (Year: 2014).*
Machine generated translation of KR 2014/0128878, published on Nov. 6, 2014 (Year: 2014).*
International Search Report, issued in PCT/JP2017/000545, PCT/ISA/210, dated Apr. 18, 2017.
Written Opinion of the International Searching Authority, issued in PCT/JP2017/000545, PCT/ISA/237, dated Apr. 18, 2017.

* cited by examiner

*Primary Examiner* — Amy C Bonaparte
(74) *Attorney, Agent, or Firm* — Birch, Stewart, Kolasch & Birch, LLP

(57) ABSTRACT

Provided is a fluorine atom-containing compound represented by formula (1) below

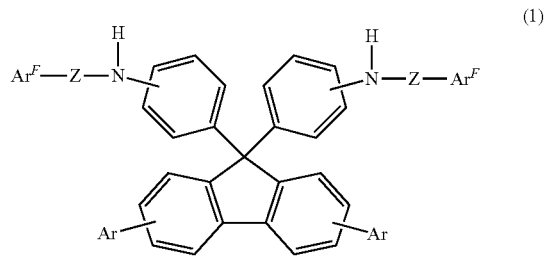

(In the formula, Z represents a predetermined divalent group, each Ar independently represents a predetermined aromatic ring-containing group, and each $Ar^F$ independently represents a predetermined fluorine atom-containing aryl group).

13 Claims, No Drawings

FLUORINE ATOM-CONTAINING COMPOUND AND USE THEREOF

TECHNICAL FIELD

The present invention relates to a fluorine atom-containing compound and to the use thereof.

BACKGROUND ART

Organic electroluminescent (EL) devices are expected to see practical application in such fields as displays and lighting. Various research is being carried out on materials and device structures with the aim of achieving such properties as low-voltage driving, high brightness and longevity.

The increased functionality of organic EL devices is being achieved via a multilayer stacked structure consisting of functional layers that are functionally discrete. Such functional layers are broadly divided by function into three types: hole-injecting/transporting layers, light-emitting layers, and electron-injecting/transporting layers. Of these, the most important function carried out by hole-injecting/transporting layers is to take hole carriers that have been injected through the anode from an external power source and transport them efficiently to the light-emitting layer. In order for these hole carriers and the electron carriers injected from the cathode side to efficiently recombine within the light-emitting layer, the function of preventing electron carriers from flowing out to the hole-injecting/transporting layer from the light-emitting layer is also required.

Film-forming processes for organic functional layers are broadly divided into dry processes such as vapor deposition and wet processes such as spin coating. On comparing these processes, wet processes are able to produce thin films having a high flatness over a large surface area, and are superior for reducing costs and achieving larger surface areas. In particular, there is a strong desire to achieve a wet process approach to the formation of a hole-injecting/transporting layer that can serve as a common layer underlying the light-emitting layer.

In light of such circumstances, the inventors have developed charge-transporting materials which give thin films capable of achieving excellent characteristics when employed in the hole-injecting layer of organic EL devices, compounds with a good solubility in organic solvents for use in such materials, and charge-transporting varnishes (Patent Documents 1 to 4).

In order to be able to impart the brightness characteristics of an organic EL device, a higher uniformity is desired not only in the hole-injecting layer but also in, for example, the hole-transporting layer (Patent Document 5). In addition, there exists a desire for a material which provides a charge-transporting thin film of excellent flatness and which can also achieve an excellent coatability for the hole-transporting layer or light-emitting layer that is formed on this film by a wet process.

PRIOR ART DOCUMENTS

Patent Documents

Patent Document 1: WO 2008/032616
Patent Document 2: WO 2008/129947
Patent Document 3: WO 2006/025342
Patent Document 4: WO 2010/058777
Patent Document 5: JP-A 2008-27646

SUMMARY OF INVENTION

Technical Problem

The present invention was arrived at in light of the above circumstances. An object of the invention is to provide compounds that are capable of giving thin films having a high hole-transporting ability and a high electron-blocking ability, and uses for such compounds.

Solution to Problem

In the course of extensive investigations aimed at achieving the above object, the inventors have discovered that thin films obtained using certain fluorine atom-containing compounds have a high hole-transporting ability and a high electron-blocking ability. This discovery ultimately led to the present invention.

Accordingly, the invention provides the following fluorine atom-containing compounds and uses therefor.

1. A fluorine atom-containing compound of formula (1) below

[Chem. 1]

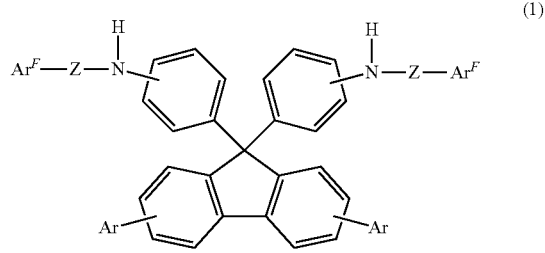

(1)

[wherein Z is a group of any of formulas (2) to (7) below

[Chem. 2]

(2)

(3)

(4)

(5)

(6)

(7)

(each $R^1$ being independently a hydrogen atom or an alkyl group of 1 to 20 carbon atoms);

each Ar is independently a group of any of formulas (8) to (11) below

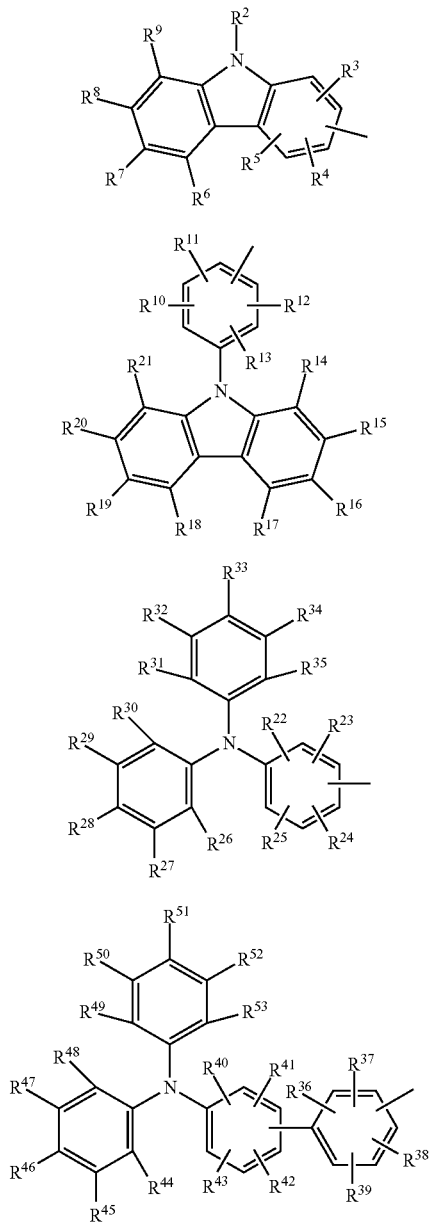

($R^2$ in formula (8) being a hydrogen atom, an alkyl group of 1 to 20 carbon atoms, an aryl group of 6 to 20 carbon atoms which may be substituted with a cyano group, a nitro group, a halogen atom, an alkyl group of 1 to 20 carbon atoms or a haloalkyl group of 1 to 20 carbon atoms, or a group of any of formulas (12) to (14) below

[Chem. 4]

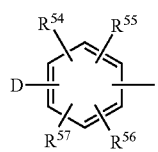

wherein D is a diarylamino group in which the aryl groups are each independently an aryl group of 6 to 20 carbon atoms; and $R^3$ to $R^{77}$ in formulas (8) to (14) being each independently a hydrogen atom, a cyano group, a nitro group, a halogen atom, an alkyl group of 1 to 20 carbon atoms or a haloalkyl group of 1 to 20 carbon atoms); and each $Ar^F$ is independently a fluoroaryl group of 6 to 20 carbon atoms which may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms; or an aryl group of 6 to 20 carbon atoms which, along with being substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, may also be substituted with a cyano group, a halogen atom or a fluoroalkoxy group of 1 to 20 carbon atoms].

2. The fluorine atom-containing compound of 1 above, wherein each $Ar^F$ is independently a phenyl group substituted with 3 or more fluorine atoms which may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms; or a 2-(trifluoromethyl)phenyl group, 3-(trifluoromethyl)phenyl group, 4-(trifluoromethyl)phenyl group, 4-ethoxy-3-(trifluoromethyl)phenyl group, 3-fluoro-4-trifluoromethylphenyl group, 4-fluoro-3-trifluoromethylphenyl group, 4-fluoro-2-trifluoromethylphenyl group, 2-fluoro-5-(trifluoromethyl)phenyl group, 3-fluoro-5-(trifluoromethyl)phenyl group, 3,5-di(trifluoromethyl)phenyl group, 2,4,6-tri(trifluoromethyl)phenyl group, 4-(pentafluoroethyl)phenyl group, 4-(3,3,3-trifluoropropyl)phenyl group, 2,3,5,6-tetrafluoro-4-trifluoromethylphenyl group, 4-(perfluorovinyl)phenyl group, 4-(perfluoropropenyl)phenyl group or 4-(perfluorobutenyl)phenyl group.

3. The fluorine atom-containing compound of 1 or 2 above, wherein the $Ar^F$ groups are identical groups.

4. The fluorine atom-containing compound of any of 1 to 3 above, wherein Z is a group of formula (2).

5. The fluorine atom-containing compound of any of 1 to 4 above, wherein $R^2$ is a phenyl group.

6. The fluorine atom-containing compound of any of 1 to 5 above, wherein $R^3$ to $R^{77}$ are hydrogen atoms.

7. A charge-transporting substance comprising the fluorine atom-containing compound of any of 1 to 6 above.

8. A charge-transporting varnish comprising the charge-transporting substance of 7 above and an organic solvent.

9. The charge-transporting varnish of 8 above, further comprising a charge-transporting substance that is free of fluorine atoms.
10. The charge-transporting varnish of 8 or 9 above, further comprising a dopant.
11. A charge-transporting thin film produced using the charge-transporting varnish of any of 8 to 10 above.
12. An organic electroluminescent device comprising the charge-transporting thin film of 11 above.
13. A method of producing a fluorine atom-containing compound of formula (1) below, which method comprises the steps of:

reacting a compound of formula (15) with a compound of formula (16) to obtain an intermediate of formula (17);

reducing the intermediate of formula (17) to obtain an intermediate of formula (18); and reacting the intermediate of formula (18) with a halide of formula (19)

[Chem. 5]

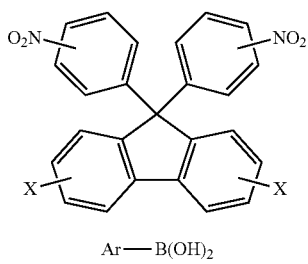
(15)

$Ar—B(OH)_2$ (16)

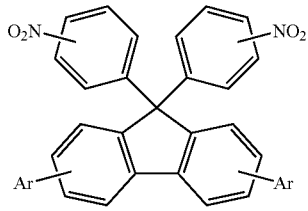
(17)

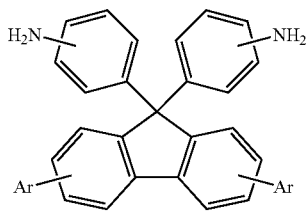
(18)

$X{\diagdown}Z{\diagdown}Ar^F$ (19)

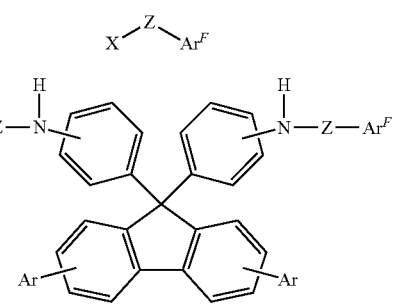
(1)

(wherein Z, Ar and $Ar^F$ are as defined above, and X is a halogen atom or a pseudo-halogen group).

Advantageous Effects of Invention

Thin films obtained using the fluorine atom-containing compounds of the invention have a high hole-transporting ability and a high electron-blocking ability, and therefore can be advantageously used as thins films for organic EL devices and other electronic devices. In particular, by employing such a thin film as a hole-injecting layer, hole-transporting layer or hole-injecting-and-transporting layer in an organic EL device, organic EL devices of excellent brightness characteristics can be obtained. Also, charge-transporting varnishes containing the fluorine atom-containing compounds of the invention can reproducibly produce thin films having excellent charge transportability even when various wet processes capable of film formation over a large surface area, such as spin coating or slit coating, are used. Moreover, the resulting thin films retain a high wettability by solvents used in the overlying layer material applied on the surface thereof. Such charge-transporting varnishes are thus capable of fully accommodating recent advances in the field of organic EL devices.

DESCRIPTION OF EMBODIMENTS

[Fluorine Atom-Containing Compound]
The fluorine atom-containing compound of the invention is a compound of formula (1) below.

[Chem. 6]

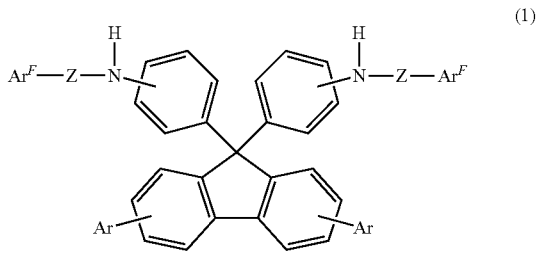
(1)

Exemplary fluorine atom-containing compounds of formula (1) include, but are not limited to, those shown below.

[Chem. 7]

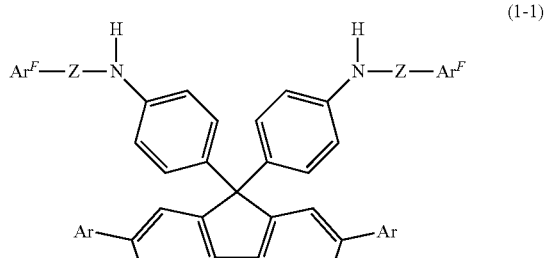
(1-1)

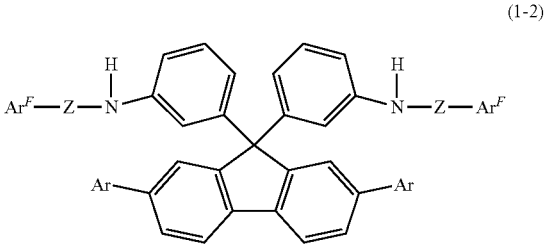
(1-2)

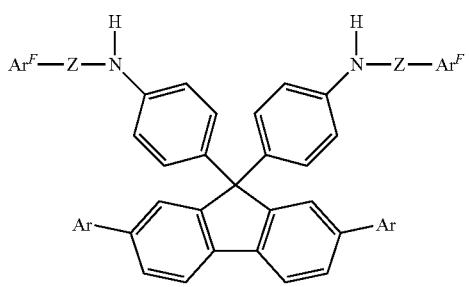

(1-3)

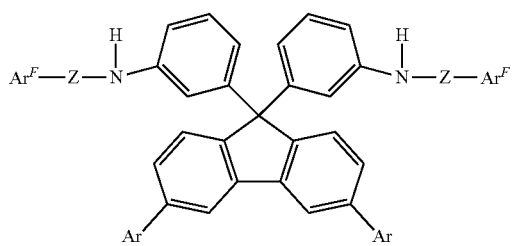

(1-4)

In formula (1), Z is a group of any one of formulas (2) to (7) below. When Z is the group of formula (4) or the group of formula (5), the carbon atom included on this group adjoins the nitrogen atom in formula (1).

[Chem. 8]

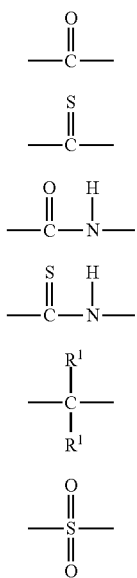

(2)
(3)
(4)
(5)
(6)
(7)

In formulas (2) to (7), each $R^1$ is independently a hydrogen atom or an alkyl group of 1 to 20 carbon atoms, with a hydrogen atom being preferred.

The alkyl group of 1 to 20 carbon atoms may be linear, branched or cyclic. Specific examples include linear or branched alkyl groups of 1 to 20 carbon atoms, such as methyl, ethyl, n-propyl, isopropyl, n-butyl, isobutyl, sec-butyl, tert-butyl, n-pentyl, n-hexyl, n-heptyl, n-octyl, n-nonyl and n-decyl groups; and cyclic alkyl groups of 3 to 20 carbon atoms such as cyclopropyl, cyclobutyl, cyclopentyl, cyclohexyl, cycloheptyl, cyclooctyl, cyclononyl, cyclo- decyl, bicyclobutyl, bicyclopentyl, bicyclohexyl, bicycloheptyl, bicyclooctyl, bicyclononyl and bicyclodecyl groups.

Z is preferably a group of formula (2), (3), (4), (5) or (6), more preferably a group of formula (2), (4) or (6), and even more preferably a group of formula (2).

In formula (1), each Ar is independently a group of any of formulas (8) to (11) below.

[Chem. 9]

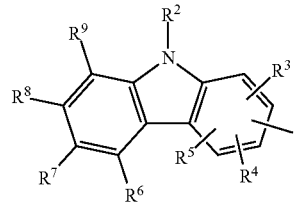

(8)

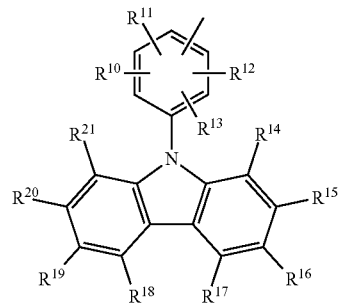

(9)

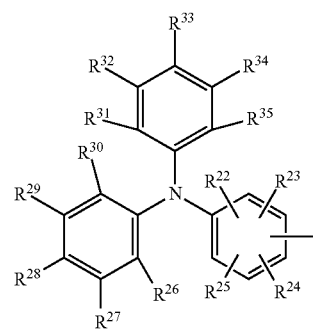

(10)

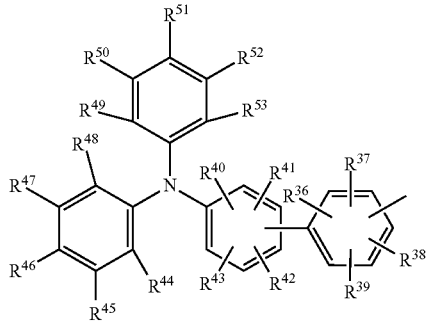

(11)

In formula (8), $R^2$ is a hydrogen atom; an alkyl group of 1 to 20 carbon atoms; an aryl group of 6 to 20 carbon atoms which may be substituted with a cyano group, a nitro group, a halogen atom, an alkyl group of 1 to 20 carbon atoms or a haloalkyl group of 1 to 20 carbon atoms; or a group of any of formulas (12) to (14) below.

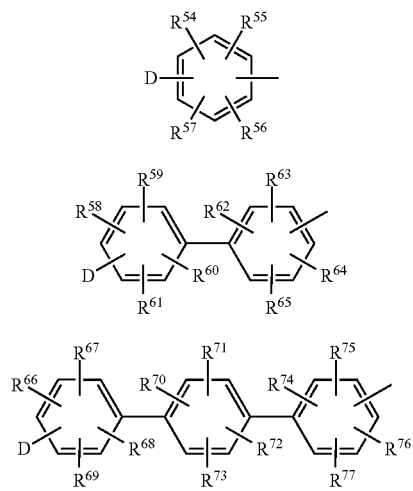

(12)

(13)

(14)

In these formulas, D is a diarylamino group wherein each aryl group is independently an aryl group of 6 to 20 carbon atoms; and $R^{54}$ to $R^{77}$ are subsequently described.

The alkyl group of 1 to 20 carbon atoms here is exemplified in the same way as that described above. Examples of the aryl group of 6 to 20 carbon atoms include phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl groups. Examples of the diarylamino group include diphenylamino, dinaphthylamino, dianthrylamino, N-phenyl-N-naphthylamino, N-phenyl-N-anthrylamino and N-naphthyl-N-anthrylamino groups.

The groups of formulas (12) to (14) are preferably ones of formulas (12-1) to (14-1) below.

[Chem. 11]

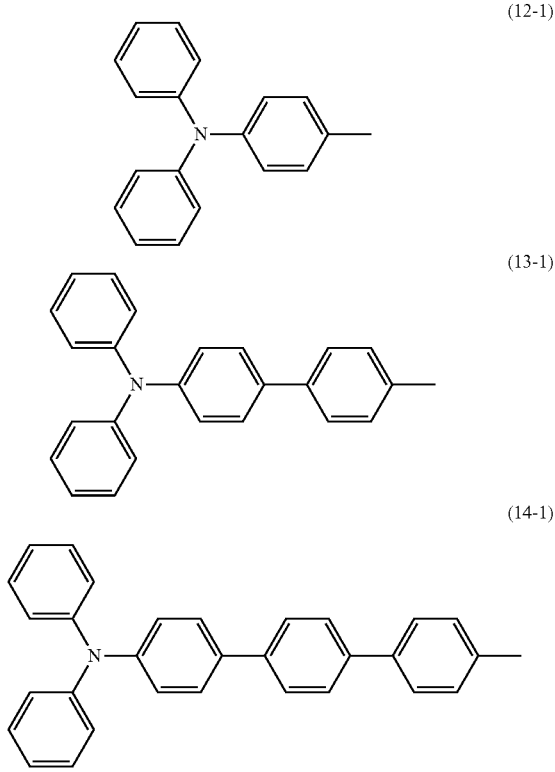

(12-1)

(13-1)

(14-1)

Of these, preferred examples of $R^2$ include a hydrogen atom, phenyl, 1-naphthyl, 2-naphthyl, 1-anthryl, 2-anthryl, 9-anthryl, 1-phenanthryl, 2-phenanthryl, 3-phenanthryl, 4-phenanthryl and 9-phenanthryl groups, groups of formula (12-1) and groups of formula (13-1). Groups of formula (12-1), groups of formula (13-1) and a phenyl group are more preferred. A phenyl group is even more preferred.

In formulas (8) to (14), $R^3$ to $R^{77}$ are each independently a hydrogen atom, a cyano group, a nitro group, a halogen atom, an alkyl group of 1 to 20 carbon atoms or a haloalkyl group of 1 to 20 carbon atoms. The alkyl group of 1 to 20 carbon atoms here is exemplified in the same way as that described above. Examples of the halogen atoms include fluorine, chlorine, bromine and iodine atoms. The haloalkyl groups are exemplified by alkyl groups in which some or all hydrogen atoms are substituted with halogen atoms. Of these, $R^3$ to $R^{77}$ are preferably hydrogen atoms, cyano groups, nitro groups, halogen atoms, alkyl groups of 1 to 10 carbon atoms or haloalkyl groups of 1 to 10 carbon atoms; more preferably hydrogen atoms, cyano groups, nitro groups, halogen atoms or trifluoromethyl groups; and even more preferably all hydrogen atoms.

The groups of formulas (8) to (11) are exemplified by, but not limited to, those shown below.

[Chem. 12]

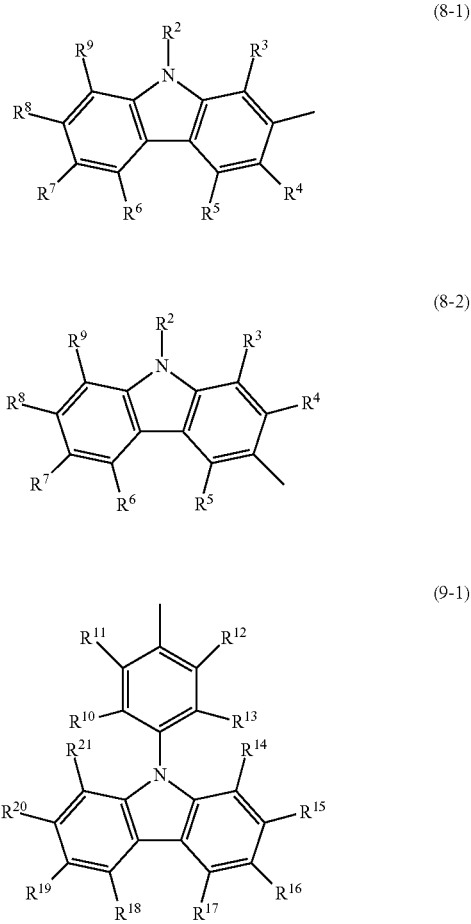

(8-1)

(8-2)

(9-1)

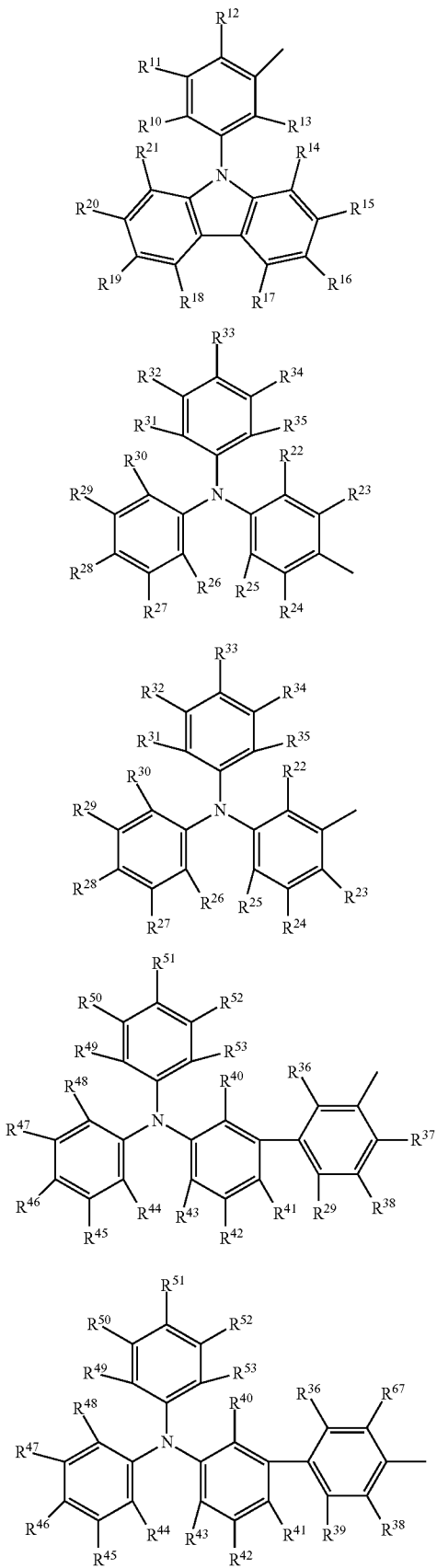

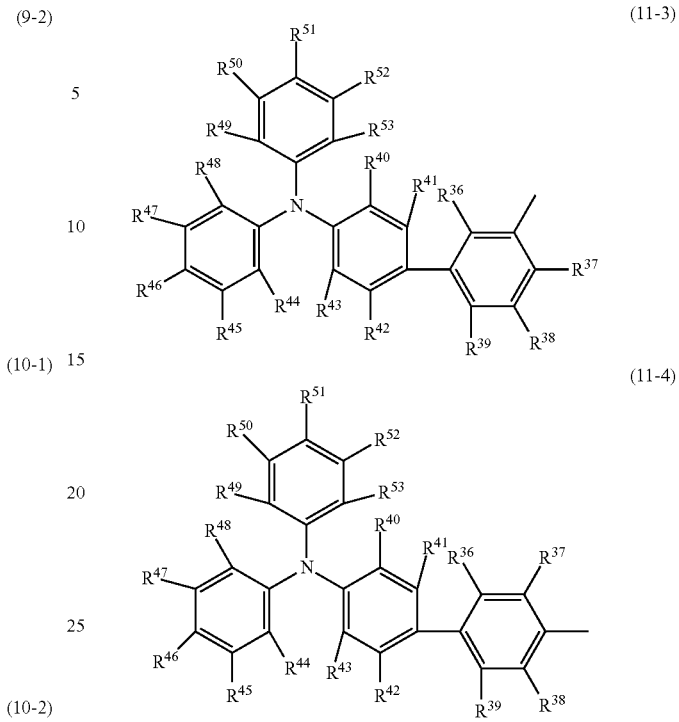

In these formulas, $R^2$ to $R^{53}$ are as defined above.

In formula (1), each $Ar^F$ is independently a fluoroaryl group of 6 to 20 carbon atoms which may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms; or an aryl group of 6 to 20 carbon atoms which, along with being substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, may also be substituted with a cyano group, a halogen atom or a fluoroalkoxy group of 1 to 20 carbon atoms.

The fluoroaryl group is not particularly limited, so long as it is an aryl group in which at least one hydrogen atom on a carbon atom is substituted with a fluorine atom. Illustrative examples include 2-fluorophenyl, 3-fluorophenyl, 4-fluorophenyl, 2,3-difluorophenyl, 2,4-difluorophenyl, 2,5-difluorophenyl, 2,6-difluorophenyl, 3,4-difluorophenyl, 3,5-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 3,4,5-trifluorophenyl, 2,3,4,5-tetrafluorophenyl, 2,3,4,6-tetrafluorophenyl, 2,3,5,6-tetrafluorophenyl, pentafluorophenyl, 2-fluoro-1-naphthyl, 3-fluoro-1-naphthyl, 4-fluoro-1-naphthyl, 6-fluoro-1-naphthyl, 7-fluoro-1-naphthyl, 8-fluoro-1-naphthyl, 4,5-difluoro-1-naphthyl, 5,7-difluoro-1-naphthyl, 5,8-difluoro-1-naphthyl, 5,6,7,8-tetrafluoro-1-naphthyl, heptafluoro-1-naphthyl, 1-fluoro-2-naphthyl, 5-fluoro-2-naphthyl, 6-fluoro-2-naphthyl, 7-fluoro-2-naphthyl, 5,7-difluoro-2-naphthyl, heptafluoro-2-naphthyl, 10-fluoro-9-anthryl, nonafluoro-1-anthryl, nonafluoro-2-anthryl, nonafluoro-9-anthryl, 9-fluoro-1-phenanthryl, 1-fluoro-9-phenanthryl, 2-fluoro-9-phenanthryl, nonafluoro-1-phenanthryl, nonafluoro-2-phenanthryl, nonafluoro-3-phenanthryl and nonafluoro-9-phenanthryl groups.

Taking into account the balance between, for example, the solubility of the fluorine atom-containing compound in organic solvents and the availability of the starting materials for the fluorine atom-containing compound, the fluoroaryl group is preferably a phenyl group which is substituted with 3 or more fluorine atoms and may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms.

The aryl group of 6 to 20 carbon atoms which, along with being substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, may also be substituted with a cyano group, a halogen atom or a fluoroalkoxy group of 1 to 20 carbon atoms (which aryl group is also referred to below, for the sake of convenience, as a "substituted aryl group") is not particularly limited, provided that it is an aryl group in which at least one hydrogen atom on a carbon atom is substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms. Illustrative examples include 2-(trifluoromethyl)phenyl, 3-(trifluoromethyl)phenyl, 4-(trifluoromethyl)phenyl, 4-ethoxy-3-(trifluoromethyl)phenyl, 3-fluoro-4-trifluoromethylphenyl, 4-fluoro-3-trifluoromethylphenyl, 4-fluoro-2-trifluoromethylphenyl, 2-fluoro-5-(trifluoromethyl)phenyl, 3-fluoro-5-(trifluoromethyl)phenyl, 3,5-di(trifluoromethyl)phenyl, 2,4,6-tri(trifluoromethyl) phenyl, 4-(pentafluoroethyl)phenyl, 4-(3,3,3-trifluoropropyl)phenyl, 2,3,5,6-tetrafluoro-4-trifluoromethylphenyl, 4-(perfluorovinyl)phenyl, 4-(perfluoropropenyl)phenyl and 4-(perfluorobutenyl)phenyl groups.

Taking into account the balance between, for example, the solubility of the fluorine atom-containing compound in organic solvents and the availability of the starting materials for the fluorine atom-containing compound, the substituted aryl group is preferably a phenyl group which, along with being substituted with a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, may also be substituted with a cyano group, a halogen atom or a fluoroalkoxy group of 1 to 20 carbon atoms (which phenyl group is also referred to below, for the sake of convenience, as a "substituted phenyl group"); more preferably a phenyl group substituted with 1 to 3 trifluoromethyl groups; and even more preferably a p-trifluoromethylphenyl group.

The fluoroalkyl group is not particularly limited, provided it is a linear or branched alkyl group in which at least one hydrogen atom on a carbon atom is substituted with a fluorine atom. Illustrative examples include fluoromethyl, difluoromethyl, trifluoromethyl, 1-fluoroethyl, 2-fluoroethyl, 1,2-difluoroethyl, 1,1-difluoroethyl, 2,2-difluoroethyl, 1,1,2-trifluoroethyl, 1,2,2-trifluoroethyl, 2,2,2-trifluoroethyl, 1,1,2,2-tetrafluoroethyl, 1,2,2,2-tetrafluoroethyl, 1,1,2,2,2-pentafluoroethyl, 1-fluoropropyl, 2-fluoropropyl, 3-fluoropropyl, 1,1-difluoropropyl, 1,2-difluoropropyl, 1,3-difluoropropyl, 2,2-difluoropropyl, 2,3-difluoropropyl, 3,3-difluoropropyl, 1,1,2-trifluoropropyl, 1,1,3-trifluoropropyl, 1,2,3-trifluoropropyl, 1,3,3-trifluoropropyl, 2,2,3-trifluoropropyl, 2,3,3-trifluoropropyl, 3,3,3-trifluoropropyl, 1,1,2,2-tetrafluoropropyl, 1,1,2,3-tetrafluoropropyl, 1,2,2,3-tetrafluoropropyl, 1,3,3,3-tetrafluoropropyl, 2,2,3,3-tetrafluoropropyl, 2,3,3,3-tetrafluoropropyl, 1,1,2,2,3-pentafluoropropyl, 1,2,2,3,3-pentafluoropropyl, 1,1,3,3,3-pentafluoropropyl, 1,2,3,3,3-pentafluoropropyl, 2,2,3,3,3-pentafluoropropyl and heptafluoropropyl groups.

The fluoroalkoxy group is not particularly limited, provided it is an alkoxy group in which at least one hydrogen atom on a carbon atom is substituted with a fluorine atom. Illustrative examples include fluoromethoxy, difluoromethoxy, trifluoromethoxy, 1-fluoroethoxy, 2-fluoroethoxy, 1,2-difluoroethoxy, 1,1-difluoroethoxy, 2,2-difluoroethoxy, 1,1,2-trifluoroethoxy, 1,2,2-trifluoroethoxy, 2,2,2-trifluoroethoxy, 1,1,2,2-tetrafluoroethoxy, 1,2,2,2-tetrafluoroethoxy, 1,1,2,2,2-pentafluoroethoxy, 1-fluoropropoxy, 2-fluoropropoxy, 3-fluoropropoxy, 1,1-difluoropropoxy, 1,2-difluoropropoxy, 1,3-difluoropropoxy, 2,2-difluoropropoxy, 2,3-difluoropropoxy, 3,3-difluoropropoxy, 1,1,2-trifluoropropoxy, 1,1,3-trifluoropropoxy, 1,2,3-trifluoropropoxy, 1,3,3-trifluoropropoxy, 2,2,3-trifluoropropoxy, 2,3,3-trifluoropropoxy, 3,3,3-trifluoropropoxy, 1,1,2,2-tetrafluoropropoxy, 1,1,2,3-tetrafluoropropoxy, 1,2,2,3-tetrafluoropropoxy, 1,3,3,3-tetrafluoropropoxy, 2,2,3,3-tetrafluoropropoxy, 2,3,3,3-tetrafluoropropoxy, 1,1,2,2,3-pentafluoropropoxy, 1,2,2,3,3-pentafluoropropoxy, 1,1,3,3,3,-pentafluoropropoxy, 1,2,3,3,3-pentafluoropropoxy, 2,2,3,3,3-pentafluoropropoxy and heptafluoropropoxy groups.

The fluorocycloalkyl group is not particularly limited, provided it is a cycloalkyl group in which at least one hydrogen atom on a carbon atom is substituted with a fluorine atom. Illustrative examples include 1-fluorocyclopropyl, 2-fluorocyclopropyl, 2,2-difluorocyclopropyl, 2,2,3,3-tetrafluorocyclopropyl, pentafluorocyclopropyl, 2,2-difluorocyclobutyl, 2,2,3,3-tetrafluorocyclobutyl, 2,2,3,3,4,4-hexafluorocyclobutyl, heptafluorocyclobutyl, 1-fluorocyclopentyl, 3-fluorocyclopentyl, 3,3-difluorocyclopentyl, 3,3,4,4-tetrafluorocyclopentyl, nonafluorocyclopentyl, 1-fluorocyclohexyl, 2-fluorocyclohexyl, 4-fluorocyclohexyl, 4,4-difluorocyclohexyl, 2,2,3,3-tetrafluorocyclohexyl, 2,3,4,5,6-pentafluorocyclohexyl and undecafluorocyclohexyl groups.

The fluorobicycloalkyl group is not particularly limited, provided it is a bicycloalkyl group in which at least one hydrogen atom on a carbon atom is substituted with a fluorine atom. Illustrative examples include 3-fluorobicyclo [1.1.0]butan-1-yl, 2,2,4,4-tetrafluorobicyclo[1.1.0]butan-1-yl, pentafluorobicyclo[1.1.0]butan-1-yl, 3-fluorobicyclo [1.1.1]pentan-1-yl, 2,2,4,4,5-pentafluorobicyclo[1.1.1] pentan-1-yl, 2,2,4,4,5,5-hexafluorobicyclo[1.1.1]pentan-1-yl, 5-fluorobicyclo[3.1.0]hexan-6-yl, 6-fluorobicyclo[3.1.0] hexan-6-yl, 6,6-difluorobicyclo[3.1.0]hexan-2-yl, 2,2,3,3,5, 5,6,6-octafluorobicyclo[2.2.0]hexan-1-yl, 1-fluorobicyclo [2.2.1]heptan-2-yl, 3-fluorobicyclo[2.2.1]heptan-2-yl, 4-fluorobicyclo[2.2.1]heptan-1-yl, 5-fluorobicyclo[3.1.1] heptan-1-yl, 1,3,3,4,5,5,6,6,7,7-decafluorobicyclo[2.2.1] heptan-2-yl, undecafluorobicyclo[2.2.1]heptan-2-yl, 3-fluorobicyclo[2.2.2]octan-1-yl and 4-fluorobicyclo[2.2.2]octan-1-yl groups.

The fluoroalkenyl group is not particularly limited, provided it is an alkenyl group in which at least one hydrogen atom on a carbon atom is substituted with a fluorine atom. Illustrative examples include 1-fluoroethenyl, 2-fluoroethenyl, 1,2-difluoroethenyl, 1,2,2-trifluoroethenyl, 2,3,3-trifluoro-1-propenyl, 3,3,3-trifluoro-1-propenyl, 2,3,3,3-tetrafluoro-1-propenyl, pentafluoro-1-propenyl, 1-fluoro-2-propenyl, 1,1-difluoro-2-propenyl, 2,3-difluoro-2-propenyl, 3,3-difluoro-2-propenyl, 2,3,3-trifluoro-2-propenyl, 1,2,3,3-tetrafluoro-2-propenyl and pentafluoro-2-propenyl groups.

The fluoroalkynyl group is not particularly limited, provided it is an alkynyl group in which at least one hydrogen atom on a carbon atom is substituted with a fluorine atom. Illustrative examples include fluoroethynyl, 3-fluoro-1-propynyl, 3,3-difluoro-1-propynyl, 3,3,3-trifluoro-1-propynyl, 1-fluoro-2-propynyl and 1,1-difluoro-2-propynyl groups.

Of these, $Ar^F$ is preferably the above-mentioned fluoroaryl groups of 6 to 20 carbon atoms which may be substituted or the above-mentioned substituted aryl group; more preferably the above-mentioned fluorophenyl groups which may be substituted or the above-mentioned substituted phenyl groups; and even more preferably the above-mentioned trifluorophenyl groups which may be substituted, the above-mentioned tetrafluorophenyl groups which may be substituted, the above-mentioned pentafluorophenyl groups which may be substituted or phenyl groups substituted with from 1 to 3 trifluoromethyl groups. From the standpoint of the ease of synthesizing the fluorine atom-containing compound, it is preferable for the $Ar^F$ groups to be identical groups.

Specific examples of groups that are suitable as $Ar^F$ include, but are not limited to, the following.

[Chem. 13]

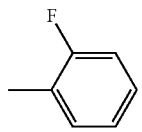
(A1)

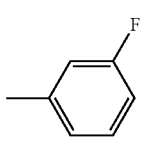
(A2)

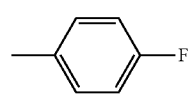
(A3)

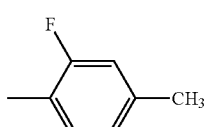
(A4)

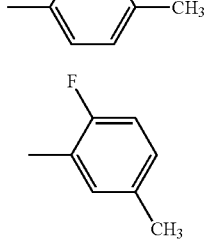
(A5)

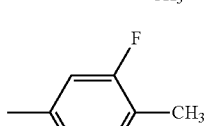
(A6)

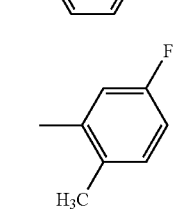
(A7)

[Chem. 14]

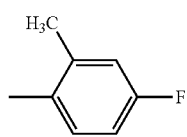
(A8)

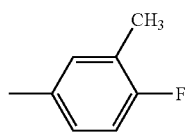
(A9)

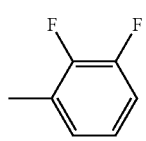
(A10)

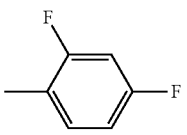
(A11)

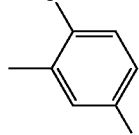
(A12)

(A13)

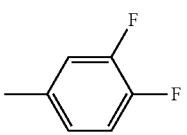
(A14)

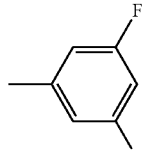
(A15)

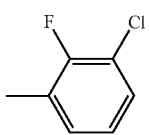
(A16)

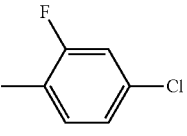
(A17)

-continued (A18)

(A19)

(A20)

(A21)

(A22)

(A23)

(A24)

(A25)

(A26)

(A27)

-continued (A28)

(A29)

(A30)

(A31)

(A32)

(A33)

(A34)

(A35)

[Chem. 15]

(A36)

(A37) (A38) (A39) (A40) (A41) (A42) (A43) (A44) (A45) (A46) (A47) (A48) (A49) (A50) (A51) (A52) (A53) (A54) (A55)

[Chem. 16]

[Chem. 17]

(A56), (A57), (A58), (A59), (A60), (A61), (A62), (A63), (A64), (A65), (A66)

[Chem. 18]

(A67), (A68), (A69), (A70), (A71), (A72), (A73), (A74)

(A75) 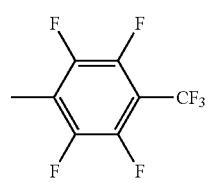
(A76) 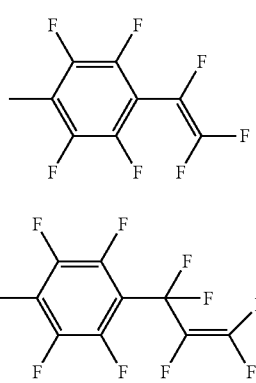
(A77) 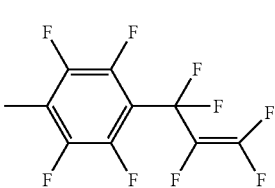
[Chem. 19]
(A78) 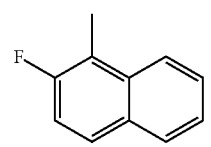
(A79) 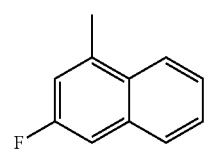
(A80) 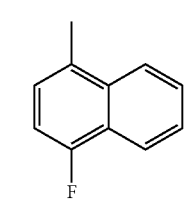
(A81) 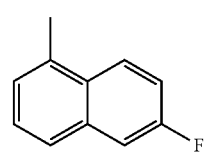
(A82) 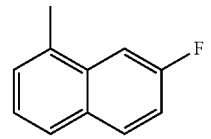
(A83) 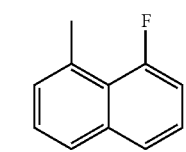
(A84) 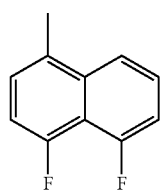
(A85) 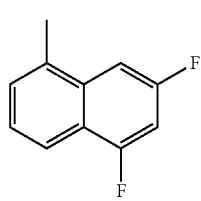
(A86) 
(A87) 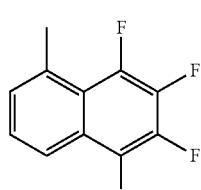
(A88) 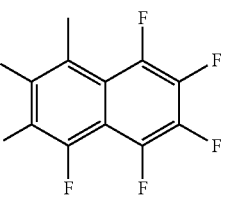
(A89) 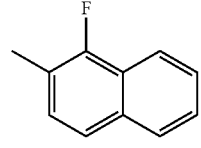
(A90) 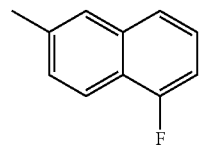
(A91) 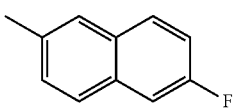

(A92) 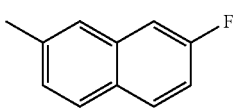
(A93) 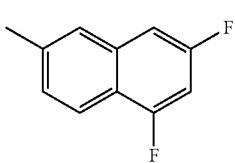
[Chem. 20]
(A94) 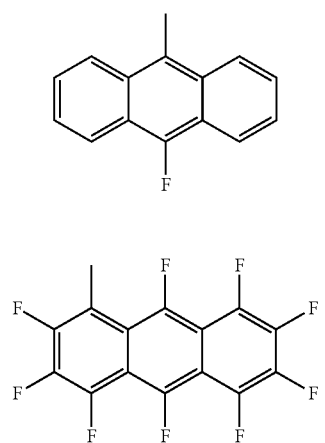
(A95)
(A96) 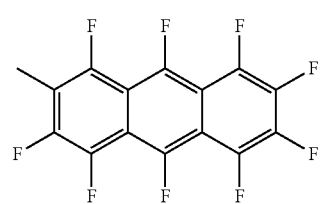
(A97) 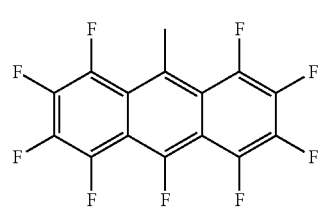
(A98) 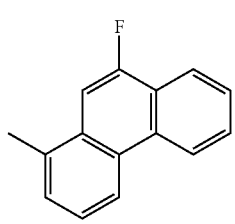
(A99) 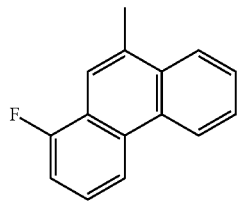
(A100) 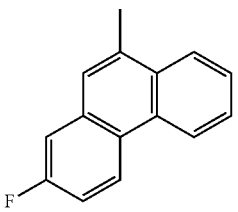
(A101) 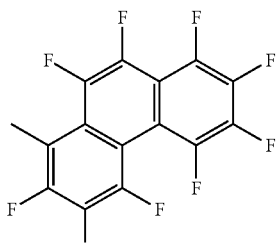
(A102) 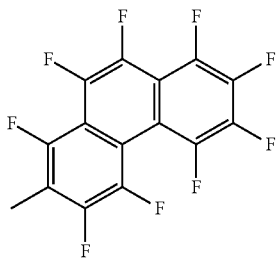
(A103) 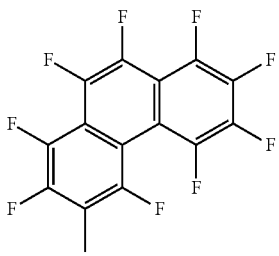
(A104) 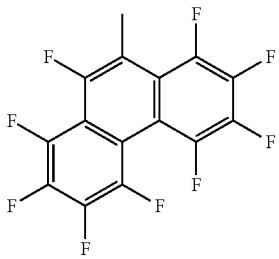
Specific examples of the fluorine atom-containing compound of formula (1) include, but are not limited to, the following.

TABLE 1

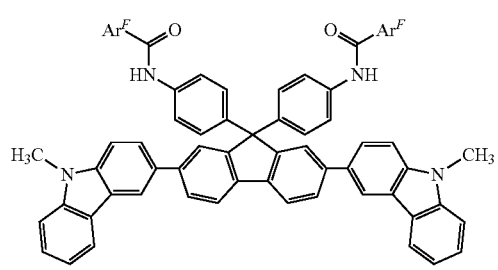

(B1)

| Compound | Ar$^F$ | Compound | Ar$^F$ |
|---|---|---|---|
| (B1-1) | (A1) | (B1-53) | (A53) |
| (B1-2) | (A2) | (B1-54) | (A54) |
| (B1-3) | (A3) | (B1-55) | (A55) |
| (B1-4) | (A4) | (B1-56) | (A56) |
| (B1-5) | (A5) | (B1-57) | (A57) |
| (B1-6) | (A6) | (B1-58) | (A58) |
| (B1-7) | (A7) | (B1-59) | (A59) |
| (B1-8) | (A8) | (B1-60) | (A60) |
| (B1-9) | (A9) | (B1-61) | (A61) |
| (B1-10) | (A10) | (B1-62) | (A62) |
| (B1-11) | (A11) | (B1-63) | (A63) |
| (B1-12) | (A12) | (B1-64) | (A64) |
| (B1-13) | (A13) | (B1-65) | (A65) |
| (B1-14) | (A14) | (B1-66) | (A66) |
| (B1-15) | (A15) | (B1-67) | (A67) |
| (B1-16) | (A16) | (B1-68) | (A68) |
| (B1-17) | (A17) | (B1-69) | (A69) |
| (B1-18) | (A18) | (B1-70) | (A70) |
| (B1-19) | (A19) | (B1-71) | (A71) |
| (B1-20) | (A20) | (B1-72) | (A72) |
| (B1-21) | (A21) | (B1-73) | (A73) |
| (B1-22) | (A22) | (B1-74) | (A74) |
| (B1-23) | (A23) | (B1-75) | (A75) |
| (B1-24) | (A24) | (B1-76) | (A76) |
| (B1-25) | (A25) | (B1-77) | (A77) |
| (B1-26) | (A26) | (B1-78) | (A78) |
| (B1-27) | (A27) | (B1-79) | (A79) |
| (B1-28) | (A28) | (B1-80) | (A80) |
| (B1-29) | (A29) | (B1-81) | (A81) |
| (B1-30) | (A30) | (B1-82) | (A82) |
| (B1-31) | (A31) | (B1-83) | (A83) |
| (B1-32) | (A32) | (B1-84) | (A84) |
| (B1-33) | (A33) | (B1-85) | (A85) |
| (B1-34) | (A34) | (B1-86) | (A86) |
| (B1-35) | (A35) | (B1-87) | (A87) |
| (B1-36) | (A36) | (B1-88) | (A88) |
| (B1-37) | (A37) | (B1-89) | (A89) |
| (B1-38) | (A38) | (B1-90) | (A90) |
| (B1-39) | (A39) | (B1-91) | (A91) |
| (B1-40) | (A40) | (B1-92) | (A92) |
| (B1-41) | (A41) | (B1-93) | (A93) |
| (B1-42) | (A42) | (B1-94) | (A94) |
| (B1-43) | (A43) | (B1-95) | (A95) |
| (B1-44) | (A44) | (B1-96) | (A96) |
| (B1-45) | (A45) | (B1-97) | (A97) |
| (B1-46) | (A46) | (B1-98) | (A98) |
| (B1-47) | (A47) | (B1-99) | (A99) |
| (B1-48) | (A48) | (B1-100) | (A100) |
| (B1-49) | (A49) | (B1-101) | (A101) |
| (B1-50) | (A50) | (B1-102) | (A102) |
| (B1-51) | (A51) | (B1-103) | (A103) |
| (B1-52) | (A52) | (B1-104) | (A104) |

TABLE 2

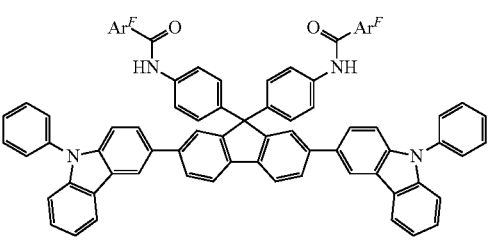

(B2)

| Compound | Ar$^F$ | Compound | Ar$^F$ |
|---|---|---|---|
| (B2-1) | (A1) | (B2-53) | (A53) |
| (B2-2) | (A2) | (B2-54) | (A54) |
| (B2-3) | (A3) | (B2-55) | (A55) |
| (B2-4) | (A4) | (B2-56) | (A56) |
| (B2-5) | (A5) | (B2-57) | (A57) |
| (B2-6) | (A6) | (B2-58) | (A58) |
| (B2-7) | (A7) | (B2-59) | (A59) |
| (B2-8) | (A8) | (B2-60) | (A60) |
| (B2-9) | (A9) | (B2-61) | (A61) |
| (B2-10) | (A10) | (B2-62) | (A62) |
| (B2-11) | (A11) | (B2-63) | (A63) |
| (B2-12) | (A12) | (B2-64) | (A64) |
| (B2-13) | (A13) | (B2-65) | (A65) |
| (B2-14) | (A14) | (B2-66) | (A66) |
| (B2-15) | (A15) | (B2-67) | (A67) |
| (B2-16) | (A16) | (B2-68) | (A68) |
| (B2-17) | (A17) | (B2-69) | (A69) |
| (B2-18) | (A18) | (B2-70) | (A70) |
| (B2-19) | (A19) | (B2-71) | (A71) |
| (B2-20) | (A20) | (B2-72) | (A72) |
| (B2-21) | (A21) | (B2-73) | (A73) |
| (B2-22) | (A22) | (B2-74) | (A74) |
| (B2-23) | (A23) | (B2-75) | (A75) |
| (B2-24) | (A24) | (B2-76) | (A76) |
| (B2-25) | (A25) | (B2-77) | (A77) |
| (B2-26) | (A26) | (B2-78) | (A78) |
| (B2-27) | (A27) | (B2-79) | (A79) |
| (B2-28) | (A28) | (B2-80) | (A80) |
| (B2-29) | (A29) | (B2-81) | (A81) |
| (B2-30) | (A30) | (B2-82) | (A82) |
| (B2-31) | (A31) | (B2-83) | (A83) |
| (B2-32) | (A32) | (B2-84) | (A84) |
| (B2-33) | (A33) | (B2-85) | (A85) |
| (B2-34) | (A34) | (B2-86) | (A86) |
| (B2-35) | (A35) | (B2-87) | (A87) |
| (B2-36) | (A36) | (B2-88) | (A88) |
| (B2-37) | (A37) | (B2-89) | (A89) |
| (B2-38) | (A38) | (B2-90) | (A90) |
| (B2-39) | (A39) | (B2-91) | (A91) |
| (B2-40) | (A40) | (B2-92) | (A92) |
| (B2-41) | (A41) | (B2-93) | (A93) |
| (B2-42) | (A42) | (B2-94) | (A94) |
| (B2-43) | (A43) | (B2-95) | (A95) |
| (B2-44) | (A44) | (B2-96) | (A96) |
| (B2-45) | (A45) | (B2-97) | (A97) |
| (B2-46) | (A46) | (B2-98) | (A98) |
| (B2-47) | (A47) | (B2-99) | (A99) |
| (B2-48) | (A48) | (B2-100) | (A100) |
| (B2-49) | (A49) | (B2-101) | (A101) |
| (B2-50) | (A50) | (B2-102) | (A102) |
| (B2-51) | (A51) | (B2-103) | (A103) |
| (B2-52) | (A52) | (B2-104) | (A104) |

TABLE 3

(B3)

| Compound | Ar$^F$ | Compound | Ar$^F$ |
|---|---|---|---|
| (B3-1) | (A1) | (B3-53) | (A53) |
| (B3-2) | (A2) | (B3-54) | (A54) |
| (B3-3) | (A3) | (B3-55) | (A55) |
| (B3-4) | (A4) | (B3-56) | (A56) |
| (B3-5) | (A5) | (B3-57) | (A57) |
| (B3-6) | (A6) | (B3-58) | (A58) |
| (B3-7) | (A7) | (B3-59) | (A59) |
| (B3-8) | (A8) | (B3-60) | (A60) |
| (B3-9) | (A9) | (B3-61) | (A61) |
| (B3-10) | (A10) | (B3-62) | (A62) |
| (B3-11) | (A11) | (B3-63) | (A63) |
| (B3-12) | (A12) | (B3-64) | (A64) |
| (B3-13) | (A13) | (B3-65) | (A65) |
| (B3-14) | (A14) | (B3-66) | (A66) |
| (B3-15) | (A15) | (B3-67) | (A67) |
| (B3-16) | (A16) | (B3-68) | (A68) |
| (B3-17) | (A17) | (B3-69) | (A69) |
| (B3-18) | (A18) | (B3-70) | (A70) |
| (B3-19) | (A19) | (B3-71) | (A71) |
| (B3-20) | (A20) | (B3-72) | (A72) |
| (B3-21) | (A21) | (B3-73) | (A73) |
| (B3-22) | (A22) | (B3-74) | (A74) |
| (B3-23) | (A23) | (B3-75) | (A75) |
| (B3-24) | (A24) | (B3-76) | (A76) |
| (B3-25) | (A25) | (B3-77) | (A77) |
| (B3-26) | (A26) | (B3-78) | (A78) |
| (B3-27) | (A27) | (B3-79) | (A79) |
| (B3-28) | (A28) | (B3-80) | (A80) |
| (B3-29) | (A29) | (B3-81) | (A81) |
| (B3-30) | (A30) | (B3-82) | (A82) |
| (B3-31) | (A31) | (B3-83) | (A83) |
| (B3-32) | (A32) | (B3-84) | (A84) |
| (B3-33) | (A33) | (B3-85) | (A85) |
| (B3-34) | (A34) | (B3-86) | (A86) |
| (B3-35) | (A35) | (B3-87) | (A87) |
| (B3-36) | (A36) | (B3-88) | (A88) |
| (B3-37) | (A37) | (B3-89) | (A89) |
| (B3-38) | (A38) | (B3-90) | (A90) |
| (B3-39) | (A39) | (B3-91) | (A91) |
| (B3-40) | (A40) | (B3-92) | (A92) |
| (B3-41) | (A41) | (B3-93) | (A93) |
| (B3-42) | (A42) | (B3-94) | (A94) |
| (B3-43) | (A43) | (B3-95) | (A95) |
| (B3-44) | (A44) | (B3-96) | (A96) |
| (B3-45) | (A45) | (B3-97) | (A97) |
| (B3-46) | (A46) | (B3-98) | (A98) |
| (B3-47) | (A47) | (B3-99) | (A99) |
| (B3-48) | (A48) | (B3-100) | (A100) |
| (B3-49) | (A49) | (B3-101) | (A101) |
| (B3-50) | (A50) | (B3-102) | (A102) |
| (B3-51) | (A51) | (B3-103) | (A103) |
| (B3-52) | (A52) | (B3-104) | (A104) |

TABLE 4

(B4)

| Compound | Ar$^F$ | Compound | Ar$^F$ |
|---|---|---|---|
| (B4-1) | (A1) | (B4-53) | (A53) |
| (B4-2) | (A2) | (B4-54) | (A54) |
| (B4-3) | (A3) | (B4-55) | (A55) |
| (B4-4) | (A4) | (B4-56) | (A56) |
| (B4-5) | (A5) | (B4-57) | (A57) |
| (B4-6) | (A6) | (B4-58) | (A58) |
| (B4-7) | (A7) | (B4-59) | (A59) |
| (B4-8) | (A8) | (B4-60) | (A60) |
| (B4-9) | (A9) | (B4-61) | (A61) |
| (B4-10) | (A10) | (B4-62) | (A62) |
| (B4-11) | (A11) | (B4-63) | (A63) |
| (B4-12) | (A12) | (B4-64) | (A64) |
| (B4-13) | (A13) | (B4-65) | (A65) |
| (B4-14) | (A14) | (B4-66) | (A66) |
| (B4-15) | (A15) | (B4-67) | (A67) |
| (B4-16) | (A16) | (B4-68) | (A68) |
| (B4-17) | (A17) | (B4-69) | (A69) |
| (B4-18) | (A18) | (B4-70) | (A70) |
| (B4-19) | (A19) | (B4-71) | (A71) |
| (B4-20) | (A20) | (B4-72) | (A72) |
| (B4-21) | (A21) | (B4-73) | (A73) |
| (B4-22) | (A22) | (B4-74) | (A74) |
| (B4-23) | (A23) | (B4-75) | (A75) |
| (B4-24) | (A24) | (B4-76) | (A76) |
| (B4-25) | (A25) | (B4-77) | (A77) |
| (B4-26) | (A26) | (B4-78) | (A78) |
| (B4-27) | (A27) | (B4-79) | (A79) |
| (B4-28) | (A28) | (B4-80) | (A80) |
| (B4-29) | (A29) | (B4-81) | (A81) |
| (B4-30) | (A30) | (B4-82) | (A82) |
| (B4-31) | (A31) | (B4-83) | (A83) |
| (B4-32) | (A32) | (B4-84) | (A84) |
| (B4-33) | (A33) | (B4-85) | (A85) |
| (B4-34) | (A34) | (B4-86) | (A86) |
| (B4-35) | (A35) | (B4-87) | (A87) |
| (B4-36) | (A36) | (B4-88) | (A88) |
| (B4-37) | (A37) | (B4-89) | (A89) |
| (B4-38) | (A38) | (B4-90) | (A90) |
| (B4-39) | (A39) | (B4-91) | (A91) |
| (B4-40) | (A40) | (B4-92) | (A92) |
| (B4-41) | (A41) | (B4-93) | (A93) |
| (B4-42) | (A42) | (B4-94) | (A94) |
| (B4-43) | (A43) | (B4-95) | (A95) |
| (B4-44) | (A44) | (B4-96) | (A96) |
| (B4-45) | (A45) | (B4-97) | (A97) |
| (B4-46) | (A46) | (B4-98) | (A98) |
| (B4-47) | (A47) | (B4-99) | (A99) |
| (B4-48) | (A48) | (B4-100) | (A100) |
| (B4-49) | (A49) | (B4-101) | (A101) |
| (B4-50) | (A50) | (B4-102) | (A102) |
| (B4-51) | (A51) | (B4-103) | (A103) |
| (B4-52) | (A52) | (B4-104) | (A104) |

TABLE 5

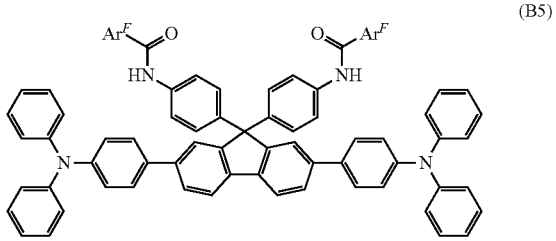

(B5)

| Compound | Ar^F | Compound | Ar^F |
|---|---|---|---|
| (B5-1) | (A1) | (B5-53) | (A53) |
| (B5-2) | (A2) | (B5-54) | (A54) |
| (B5-3) | (A3) | (B5-55) | (A55) |
| (B5-4) | (A4) | (B5-56) | (A56) |
| (B5-5) | (A5) | (B5-57) | (A57) |
| (B5-6) | (A6) | (B5-58) | (A58) |
| (B5-7) | (A7) | (B5-59) | (A59) |
| (B5-8) | (A8) | (B5-60) | (A60) |
| (B5-9) | (A9) | (B5-61) | (A61) |
| (B5-10) | (A10) | (B5-62) | (A62) |
| (B5-11) | (A11) | (B5-63) | (A63) |
| (B5-12) | (A12) | (B5-64) | (A64) |
| (B5-13) | (A13) | (B5-65) | (A65) |
| (B5-14) | (A14) | (B5-66) | (A66) |
| (B5-15) | (A15) | (B5-67) | (A67) |
| (B5-16) | (A16) | (B5-68) | (A68) |
| (B5-17) | (A17) | (B5-69) | (A69) |
| (B5-18) | (A18) | (B5-70) | (A70) |
| (B5-19) | (A19) | (B5-71) | (A71) |
| (B5-20) | (A20) | (B5-72) | (A72) |
| (B5-21) | (A21) | (B5-73) | (A73) |
| (B5-22) | (A22) | (B5-74) | (A74) |
| (B5-23) | (A23) | (B5-75) | (A75) |
| (B5-24) | (A24) | (B5-76) | (A76) |
| (B5-25) | (A25) | (B5-77) | (A77) |
| (B5-26) | (A26) | (B5-78) | (A78) |
| (B5-27) | (A27) | (B5-79) | (A79) |
| (B5-28) | (A28) | (B5-80) | (A80) |
| (B5-29) | (A29) | (B5-81) | (A81) |
| (B5-30) | (A30) | (B5-82) | (A82) |
| (B5-31) | (A31) | (B5-83) | (A83) |
| (B5-32) | (A32) | (B5-84) | (A84) |
| (B5-33) | (A33) | (B5-85) | (A85) |
| (B5-34) | (A34) | (B5-86) | (A86) |
| (B5-35) | (A35) | (B5-87) | (A87) |
| (B5-36) | (A36) | (B5-88) | (A88) |
| (B5-37) | (A37) | (B5-89) | (A89) |
| (B5-38) | (A38) | (B5-90) | (A90) |
| (B5-39) | (A39) | (B5-91) | (A91) |
| (B5-40) | (A40) | (B5-92) | (A92) |
| (B5-41) | (A41) | (B5-93) | (A93) |
| (B5-42) | (A42) | (B5-94) | (A94) |
| (B5-43) | (A43) | (B5-95) | (A95) |
| (B5-44) | (A44) | (B5-96) | (A96) |
| (B5-45) | (A45) | (B5-97) | (A97) |
| (B5-46) | (A46) | (B5-98) | (A98) |
| (B5-47) | (A47) | (B5-99) | (A99) |
| (B5-48) | (A48) | (B5-100) | (A100) |
| (B5-49) | (A49) | (B5-101) | (A101) |
| (B5-50) | (A50) | (B5-102) | (A102) |
| (B5-51) | (A51) | (B5-103) | (A103) |
| (B5-52) | (A52) | (B5-104) | (A104) |

TABLE 6

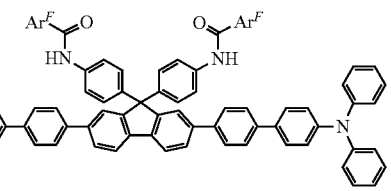

(B6)

| Compound | Ar^F | Compound | Ar^F |
|---|---|---|---|
| (B6-1) | (A1) | (B6-53) | (A53) |
| (B6-2) | (A2) | (B6-54) | (A54) |
| (B6-3) | (A3) | (B6-55) | (A55) |
| (B6-4) | (A4) | (B6-56) | (A56) |
| (B6-5) | (A5) | (B6-57) | (A57) |
| (B6-6) | (A6) | (B6-58) | (A58) |
| (B6-7) | (A7) | (B6-59) | (A59) |
| (B6-8) | (A8) | (B6-60) | (A60) |
| (B6-9) | (A9) | (B6-61) | (A61) |
| (B6-10) | (A10) | (B6-62) | (A62) |
| (B6-11) | (A11) | (B6-63) | (A63) |
| (B6-12) | (A12) | (B6-64) | (A64) |
| (B6-13) | (A13) | (B6-65) | (A65) |
| (B6-14) | (A14) | (B6-66) | (A66) |
| (B6-15) | (A15) | (B6-67) | (A67) |
| (B6-16) | (A16) | (B6-68) | (A68) |
| (B6-17) | (A17) | (B6-69) | (A69) |
| (B6-18) | (A18) | (B6-70) | (A70) |
| (B6-19) | (A19) | (B6-71) | (A71) |
| (B6-20) | (A20) | (B6-72) | (A72) |
| (B6-21) | (A21) | (B6-73) | (A73) |
| (B6-22) | (A22) | (B6-74) | (A74) |
| (B6-23) | (A23) | (B6-75) | (A75) |
| (B6-24) | (A24) | (B6-76) | (A76) |
| (B6-25) | (A25) | (B6-77) | (A77) |
| (B6-26) | (A26) | (B6-78) | (A78) |
| (B6-27) | (A27) | (B6-79) | (A79) |
| (B6-28) | (A28) | (B6-80) | (A80) |
| (B6-29) | (A29) | (B6-81) | (A81) |
| (B6-30) | (A30) | (B6-82) | (A82) |
| (B6-31) | (A31) | (B6-83) | (A83) |
| (B6-32) | (A32) | (B6-84) | (A84) |
| (B6-33) | (A33) | (B6-85) | (A85) |
| (B6-34) | (A34) | (B6-86) | (A86) |
| (B6-35) | (A35) | (B6-87) | (A87) |
| (B6-36) | (A36) | (B6-88) | (A88) |
| (B6-37) | (A37) | (B6-89) | (A89) |
| (B6-38) | (A38) | (B6-90) | (A90) |
| (B6-39) | (A39) | (B6-91) | (A91) |
| (B6-40) | (A40) | (B6-92) | (A92) |
| (B6-41) | (A41) | (B6-93) | (A93) |
| (B6-42) | (A42) | (B6-94) | (A94) |
| (B6-43) | (A43) | (B6-95) | (A95) |
| (B6-44) | (A44) | (B6-96) | (A96) |
| (B6-45) | (A45) | (B6-97) | (A97) |
| (B6-46) | (A46) | (B6-98) | (A98) |
| (B6-47) | (A47) | (B6-99) | (A99) |
| (B6-48) | (A48) | (B6-100) | (A100) |
| (B6-49) | (A49) | (B6-101) | (A101) |
| (B6-50) | (A50) | (B6-102) | (A102) |
| (B6-51) | (A51) | (B6-103) | (A103) |
| (B6-52) | (A52) | (B6-104) | (A104) |

[Method of Synthesizing Fluorine Atom-Containing Compound]

The fluorine atom-containing compound of the invention can be synthesized by the method shown in Scheme A below.

[Chem. 21]

Scheme A

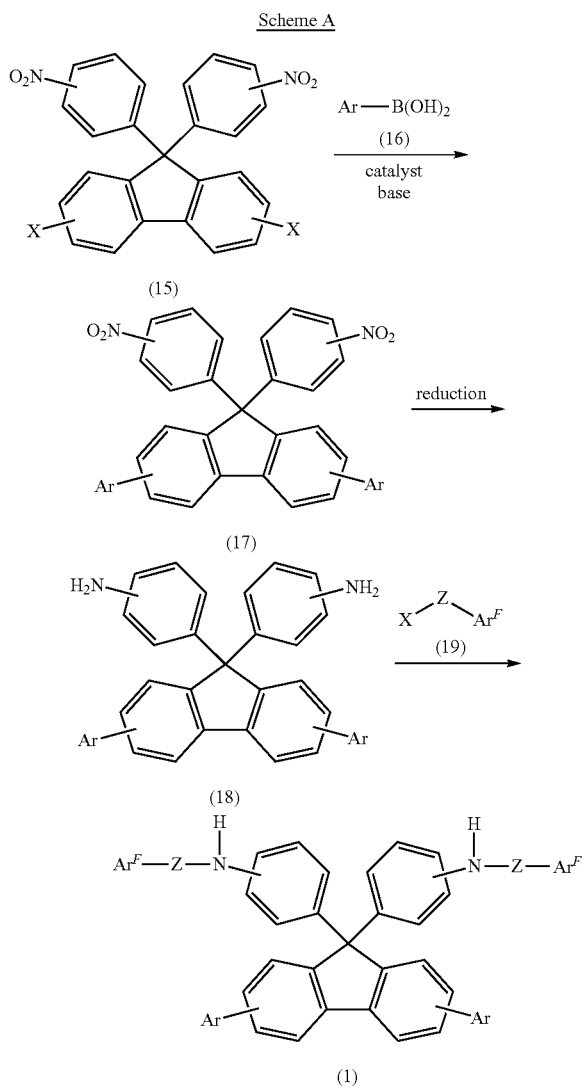

Here, Z, Ar and $Ar^F$ are as defined above. X is a halogen atom or a pseudo-halogen group.

Examples of the halogen atom include fluorine, chlorine, bromine and iodine atoms. Examples of the pseudo-halogen group include the methanesulfonyloxy group, fluoroalkylsulfonyloxy groups such as the trifluoromethanesulfonyloxy and nonafluorobutanesulfonyloxy groups, and aromatic sulfonyloxy groups such as the benzenesulfonyloxy and toluenesulfonyloxy groups.

The compound of formula (15) can be synthesized by a hitherto known method. For example, it can be synthesized in accordance with the method described in *J. Mater. Chem. C*, 2014, pp. 1068-1075.

In Scheme A, the first step is the step of obtaining an intermediate of formula (17) from a compound of formula (15) and a compound of formula (16) via a coupling reaction. Scheme A shows, by way of illustration, a synthesis method that utilizes the Suzuki-Miyaura coupling reaction, although synthesis utilizing another coupling reaction is also possible.

The catalyst used in the Suzuki-Miyaura coupling reaction is exemplified by palladium catalysts such as [1,1'-bis (diphenylphosphino)ferrocene]palladium(II) dichloride ($PdCl_2(dppf)$), tetrakis(triphenylphosphine)palladium ($Pd(PPh_3)_4$), bis(triphenylphosphine)dichloropalladium ($Pd(PPh_3)_2Cl_2$), bis(benzylideneacetone)palladium ($Pd(dba)_2$), tris(benzylideneacetone)dipalladium ($Pd_2(dba)_3$), bis(tri-tert-butylphosphine)palladium ($Pd(P-t-Bu_3)_2$) and palladium acetate ($Pd(OAc)_2$). Of these, from the standpoint of efficiently obtaining the target substance, preferred catalysts are $PdCl_2(dppf)$, $Pd(PPh_3)_4$, $Pd(PPh_3)_2Cl_2$ and $Pd(P-t-Bu_3)_2$, with $Pd(PPh_3)_4$ and $Pd(P-t-Bu_3)_2$ being more preferred. The amount of the catalyst used, based on the compound of formula (15), is generally from about 0.1 mol % to about 50 mol %, preferably from 0.1 to 30 mol %, and more preferably from 1 to 10 mol %.

A base is also used in the Suzuki-Miyaura coupling reaction. Examples of the base include hydroxides such as sodium hydroxide, potassium hydroxide and cesium hydroxide; alkoxides such as sodium tert-butoxide and potassium tert-butoxide; fluorides such as lithium fluoride, potassium fluoride and cesium fluoride; carbonates such as lithium carbonate, sodium carbonate, potassium carbonate, cesium carbonate, sodium bicarbonate and potassium bicarbonate; phosphates such as potassium phosphate; and amines such as trimethylamine, triethylamine, diisopropylamine, n-butylamine and diisopropylethylamine. Of these, from the standpoint of efficiently obtaining the target substance, preferred bases are carbonates such as sodium carbonate, potassium carbonate, cesium carbonate, sodium bicarbonate and potassium bicarbonate, and phosphates such as potassium phosphate; potassium carbonate and cesium carbonate are more preferred. The amount of the base used with respect to the compound of formula (15) is generally from about 2 equivalents to about 20 equivalents, preferably from 1 to 20 equivalents, and more preferably from 2 to 8 equivalents.

The solvent used in the first step is not particularly limited, provided that it does not have an adverse effect on the reaction. Specific examples include aliphatic hydrocarbons (pentane, n-hexane, n-octane, n-decane, decalin, etc.), halogenated aliphatic hydrocarbons (chloroform, dichloromethane, dichloroethane, carbon tetrachloride, etc.), aromatic hydrocarbons (benzene, nitrobenzene, toluene, o-xylene, m-xylene, p-xylene, mesitylene, etc.), ethers (diethyl ether, diisopropyl ether, tert-butyl methyl ether, tetrahydrofuran (THF), dioxane, 1,2-dimethoxyethane, 1,2-diethoxyethane, etc.), amides (N,N-dimethylformamide (DMF), N,N-dimethylacetamide, etc.), lactams and lactones (N-methylpyrrolidone, γ-butyrolactone, etc.), urea derivatives (N,N-dimethylimidazolidinone, tetramethylurea, etc.), sulfoxides (dimethylsulfoxide, sulfolane, etc.), and nitriles (acetonitrile, propionitrile, butyronitrile, etc.). Of these, from the standpoint of efficiently obtaining the target substance, preferred solvents include aliphatic hydrocarbons (pentane, n-hexane, n-octane, n-decane, decalin, etc.), aromatic hydrocarbons (benzene, nitrobenzene, toluene, o-xylene, m-xylene, p-xylene, mesitylene, etc.), and ethers (diethyl ether, diisopropyl ether, tert-butyl methyl ether, THF, dioxane, 1,2-dimethoxyethane, 1,2-diethoxyethane, etc.). Aromatic hydrocarbons (benzene, nitrobenzene, toluene, o-xylene, m-xylene, p-xylene, mesitylene, etc.) and ethers (diethyl ether, diisopropyl ether, tert-butyl methyl ether, THF, dioxane, 1,2-dimethoxyethane, 1,2-diethoxyethane, etc.) are even more preferred.

The charging ratio between the compound of formula (15) and the compound of formula (16) is such that the amount of the compound of formula (16) with respect to the compound of formula (15) is preferably from 2 to 6 equivalents, and more preferably from 2 to 3 equivalents.

In the first step, the reaction temperature is suitably set within the range of the solvent melting point to the solvent boiling point while taking into account the types and amounts of the starting compounds and catalyst used, and is typically from about 0° C. to about 200° C., and preferably from 0° C. to 50° C. The reaction time differs according to such factors as the starting compounds used and the reaction temperature, and therefore cannot be strictly specified, but is generally from about 1 hour to about 24 hours.

In Scheme A, the second step is the step of reducing the intermediate of formula (17) to obtain an intermediate of formula (18). The method of reduction is exemplified by known methods such as catalytic hydrogenation and chemical reduction using a metal and an acid.

When reduction is carried out by catalytic hydrogenation, it may be carried out using a known catalyst such as palladium on carbon, Raney nickel catalyst, platinum oxide, ruthenium on carbon, rhodium on carbon or platinum on carbon. Examples of the catalytic hydrogenation conditions include a hydrogen pressure of from 1 to 10 atmospheres, a reaction temperature of from 20 to 100° C. and a reaction time of from 1 to 48 hours.

In Scheme A, the third step is the step of reacting the intermediate of formula (18) with a compound of formula (19) to synthesize a fluorine atom-containing compound of formula (1).

Examples of compounds of formula (19) in which Z is a group of formula (2) include, but are not limited to, 2-fluorobenzoyl chloride, 3-fluorobenzoyl chloride, 4-fluorobenzoyl chloride, 2-fluoro-4-methylbenzoyl chloride, 2-fluoro-5-methylbenzoyl chloride, 3-fluoro-4-methylbenzoyl chloride, 3-fluoro-6-methylbenzoyl chloride, 4-fluoro-2-methylbenzoyl chloride, 4-fluoro-3-methylbenzoyl chloride, 2,3-difluorobenzoyl chloride, 2,4-difluorobenzoyl chloride, 2,5-difluorobenzoyl chloride, 2,6-difluorobenzoyl chloride, 3,4-difluorobenzoyl chloride, 3,5-difluorobenzoyl chloride, 3-chloro-2-fluorobenzoyl chloride, 4-chloro-2-fluorobenzoyl chloride, 5-chloro-2-fluorobenzoyl chloride, 2-chloro-6-fluorobenzoyl chloride, 2-chloro-3-fluorobenzoyl chloride, 2-chloro-4-fluorobenzoyl chloride, 2-chloro-5-fluorobenzoyl chloride, 3-chloro-4-fluorobenzoyl chloride, 3-chloro-5-fluorobenzoyl chloride, 3-bromo-2-fluorobenzoyl chloride, 4-bromo-2-fluorobenzoyl chloride, 5-bromo-2-fluorobenzoyl chloride, 2-bromo-6-fluorobenzoyl chloride, 2-bromo-3-fluorobenzoyl chloride, 2-bromo-4-fluorobenzoyl chloride, 2-bromo-5-fluorobenzoyl chloride, 3-bromo-4-fluorobenzoyl chloride, 3-bromo-5-fluorobenzoyl chloride, 2-fluoro-5-iodobenzoyl chloride, 2-fluoro-6-iodobenzoyl chloride, 2-fluoro-3-(trifluoromethyl)benzoyl chloride, 2-fluoro-5-(trifluoromethyl)benzoyl chloride, 2-fluoro-6-(trifluoromethyl)benzoyl chloride, 3-fluoro-4-(trifluoromethyl)benzoyl chloride, 3-fluoro-5-(trifluoromethyl)benzoyl chloride, 3-fluoro-6-(trifluoromethyl)benzoyl chloride, 4-fluoro-2-(trifluoromethyl)benzoyl chloride, 4-fluoro-3-(trifluoromethyl)benzoyl chloride, 2-fluoro-4-nitrobenzoyl chloride, 2-fluoro-5-nitrobenzoyl chloride, 3-fluoro-2-nitrobenzoyl chloride, 3-fluoro-4-nitrobenzoyl chloride, 3-fluoro-6-nitrobenzoyl chloride, 4-fluoro-2-nitrobenzoyl chloride, 4-fluoro-3-nitrobenzoyl chloride, 4-cyano-2-fluorobenzoyl chloride, 3-cyano-5-fluorobenzoyl chloride, 2,3,4-trifluorobenzoyl chloride, 2,3,5-trifluorobenzoyl chloride, 2,3,6-trifluorobenzoyl chloride, 2,4,5-trifluorobenzoyl chloride, 2,4,6-trifluorobenzoyl chloride, 3,4,5-trifluorobenzoyl chloride, 4-chloro-2,4-difluorobenzoyl chloride, 2,4-dichloro-5-fluoro-4-nitrobenzoyl chloride, 2,4,5-trifluoro-3-methyl-6-nitrobenzoyl chloride, 2,3,4,5-tetrafluorobenzoyl chloride, 2,3,5,6-tetrafluorobenzoyl chloride, 2,3,5,6-tetrafluoro-4-methylbenzoyl chloride, 2,3,4,5-tetrafluoro-6-nitrobenzoyl chloride, 2,3,4,5,6-pentafluorobenzoyl chloride, 2-(trifluoromethyl)benzoyl chloride, 3-(trifluoromethyl)benzoyl chloride, 4-(trifluoromethyl)benzoyl chloride, 3-trifluoromethyl-4-ethoxybenzoyl chloride, 3,5-bis(trifluoromethyl)benzoyl chloride, 2,4,6-tris(trifluoromethyl)benzoyl chloride, 4-(pentafluoroethyl)benzoyl chloride, 4-(3-tetrafluoropropyl)benzoyl chloride, 2,3,5,6-tetrafluoro-4-(trifluoromethyl)benzoyl chloride, 2,3,5,6-tetrafluoro-4-(trifluorovinyl)benzoyl chloride and 2,3,5,6-tetrafluoro-4-(pentafluoroallyl)benzoyl chloride.

Examples of compounds of formula (19) in which Z is a group of formula (3) include, but are not limited to, 2-fluorothiobenzoyl chloride, 3-fluorothiobenzoyl chloride, 4-fluorothiobenzoyl chloride, 2-fluoro-4-methylthiobenzoyl chloride, 2-fluoro-5-methylthiobenzoyl chloride, 3-fluoro-4-methylthiobenzoyl chloride, 3-fluoro-6-methylthiobenzoyl chloride, 4-fluoro-2-methylthiobenzoyl chloride, 4-fluoro-3-methylthiobenzoyl chloride, 2,3-difluorothiobenzoyl chloride, 2,4-difluorothiobenzoyl chloride, 2,5-difluorothiobenzoyl chloride, 2,6-difluorothiobenzoyl chloride, 3,4-difluorothiobenzoyl chloride, 3,5-difluorothiobenzoyl chloride, 3-chloro-2-fluorothiobenzoyl chloride, 4-chloro-2-fluorothiobenzoyl chloride, 5-chloro-2-fluorothiobenzoyl chloride, 2-chloro-6-fluorothiobenzoyl chloride, 2-chloro-3-fluorothiobenzoyl chloride, 2-chloro-4-fluorothiobenzoyl chloride, 2-chloro-5-fluorothiobenzoyl chloride, 3-chloro-4-fluorothiobenzoyl chloride, 3-chloro-5-fluorothiobenzoyl chloride, 3-bromo-2-fluorothiobenzoyl chloride, 4-bromo-2-fluorothiobenzoyl chloride, 5-bromo-2-fluorothiobenzoyl chloride, 2-bromo-6-fluorothiobenzoyl chloride, 2-bromo-3-fluorothiobenzoyl chloride, 2-bromo-4-fluorothiobenzoyl chloride, 2-bromo-5-fluorothiobenzoyl chloride, 3-bromo-4-fluorothiobenzoyl chloride, 3-bromo-5-fluorothiobenzoyl chloride, 2-fluoro-5-iodothiobenzoyl chloride, 2-fluoro-6-iodothiobenzoyl chloride, 2-fluoro-3-(trifluoromethyl)thiobenzoyl chloride, 2-fluoro-5-(trifluoromethyl)thiobenzoyl chloride, 2-fluoro-6-(trifluoromethyl)thiobenzoyl chloride, 3-fluoro-4-(trifluoromethyl)thiobenzoyl chloride, 3-fluoro-5-(trifluoromethyl)thiobenzoyl chloride, 3-fluoro-6-(trifluoromethyl)thiobenzoyl chloride, 4-fluoro-2-(trifluoromethyl)thiobenzoyl chloride, 4-fluoro-3-(trifluoromethyl)thiobenzoyl chloride, 2-fluoro-4-nitrothiobenzoyl chloride, 2-fluoro-5-nitrothiobenzoyl chloride, 3-fluoro-2-nitrothiobenzoyl chloride, 3-fluoro-4-nitrothiobenzoyl chloride, 3-fluoro-6-nitrothiobenzoyl chloride, 4-fluoro-2-nitrothiobenzoyl chloride, 4-fluoro-3-nitrothiobenzoyl chloride, 4-cyano-2-fluorothiobenzoyl chloride, 3-cyano-5-fluorothiobenzoyl chloride, 2,3,4-trifluorothiobenzoyl chloride, 2,3,5-trifluorothiobenzoyl chloride, 2,3,6-trifluorothiobenzoyl chloride, 2,4,5-trifluorothiobenzoyl chloride, 2,4,6-trifluorothiobenzoyl chloride, 3,4,5-trifluorothiobenzoyl chloride, 4-chloro-2,4-difluorothiobenzoyl chloride, 2,4-dichloro-5-fluoro-4-nitrothiobenzoyl chloride, 2,4,5-trifluoro-3-methyl-6-nitrothiobenzoyl chloride, 2,3,4,5-tetrafluorothiobenzoyl chloride, 2,3,5,6-tetrafluorothiobenzoyl chloride, 2,3,5,6-tetrafluoro-4-methylthiobenzoyl chloride, 2,3,4,5-tetrafluoro-6-nitrothiobenzoyl chloride, 2,3,4,5,6-pentafluorothiobenzoyl chloride, 2-(trifluoromethyl)thiobenzoyl chloride, 3-(trifluoromethyl)thiobenzoyl chloride, 4-(trifluoromethyl)thiobenzoyl chloride, 3-trifluoromethyl-4-ethoxythiobenzoyl chloride, 3,5-bis(trifluoromethyl)thiobenzoyl chloride, 2,4,6-tris(trifluoromethyl)thiobenzoyl chloride, 4-(pentafluoroethyl)thiobenzoyl chloride, 4-(3-tetrafluoropropyl)thiobenzoyl chloride, 2,3,5,6-tetrafluoro-4-(trifluoromethyl)thiobenzoyl chloride, 2,3,5,6-tetrafluoro-4-(trifluorovinyl)thiobenzoyl chloride and 2,3,5,6-tetrafluoro-4-(pentafluoroallyl)thiobenzoyl chloride.

Examples of compounds of formula (19) in which Z is a group of formula (4) include, but are not limited to, 2-fluorophenylcarbamoyl chloride, 3-fluorophenylcarbamoyl chloride, 4-fluorophenylcarbamoyl chloride, 2-fluoro-4-methylphenylcarbamoyl chloride, 2-fluoro-5-methylphenylcarbamoyl chloride, 3-fluoro-4-methylphenylcarbamoyl chloride, 3-fluoro-6-methylphenylcarbamoyl chloride, 4-fluoro-2-methylphenylcarbamoyl chloride, 4-fluoro-3-methylphenylcarbamoyl chloride, 2,3-difluorophenylcarbamoyl chloride, 2,4-difluorophenylcarbamoyl chloride, 2,5-difluorophenylcarbamoyl chloride, 2,6-difluorophenylcarbamoyl chloride, 3,4-difluorophenylcarbamoyl chloride, 3,5-difluorophenylcarbamoyl chloride, 3-chloro-2-fluorophenylcarbamoyl chloride, 4-chloro-2-fluorophenylcarbamoyl chloride, 5-chloro-2-fluorophenylcarbamoyl chloride, 2-chloro-6-fluorophenylcarbamoyl chloride, 2-chloro-3-fluorophenylcarbamoyl chloride, 2-chloro-4-fluorophenylcarbamoyl chloride, 2-chloro-5-fluorophenylcarbamoyl chloride, 3-chloro-4-fluorophenylcarbamoyl chloride, 3-chloro-5-fluorophenylcarbamoyl chloride, 3-bromo-2-fluorophenylcarbamoyl chloride, 4-bromo-2-fluorophenylcarbamoyl chloride, 5-bromo-2-fluorophenylcarbamoyl chloride, 2-bromo-6-fluorophenylcarbamoyl chloride, 2-bromo-3-fluorophenylcarbamoyl chloride, 2-bromo-4-fluorophenylcarbamoyl chloride, 2-bromo-5-fluorophenylcarbamoyl chloride, 3-bromo-4-fluorophenylcarbamoyl chloride, 3-bromo-5-fluorophenylcarbamoyl chloride, 2-fluoro-5-iodophenylcarbamoyl chloride, 2-fluoro-6-iodophenylcarbamoyl chloride, 2-fluoro-3-(trifluoromethyl)phenylcarbamoyl chloride, 2-fluoro-5-(trifluoromethyl)phenylcarbamoyl chloride, 2-fluoro-6-(trifluoromethyl)phenylcarbamoyl chloride, 3-fluoro-4-(trifluoromethyl)phenylcarbamoyl chloride, 3-fluoro-5-(trifluoromethyl)phenylcarbamoyl chloride, 3-fluoro-6-(trifluoromethyl)phenylcarbamoyl chloride, 4-fluoro-2-(trifluoromethyl)phenylcarbamoyl chloride, 4-fluoro-3-(trifluoromethyl)phenylcarbamoyl chloride, 2-fluoro-4-nitrophenylcarbamoyl chloride, 2-fluoro-5-nitrophenylcarbamoyl chloride, 3-fluoro-2-nitrophenylcarbamoyl chloride, 3-fluoro-4-nitrophenylcarbamoyl chloride, 3-fluoro-6-nitrophenylcarbamoyl chloride, 4-fluoro-2-nitrophenylcarbamoyl chloride, 4-fluoro-3-nitrophenylcarbamoyl chloride, 4-cyano-2-fluorophenylcarbamoyl chloride, 3-cyano-5-fluorophenylcarbamoyl chloride, 2,3,4-trifluorophenylcarbamoyl chloride, 2,3,5-trifluorophenylcarbamoyl chloride, 2,3,6-trifluorophenylcarbamoyl chloride, 2,4,5-trifluorophenylcarbamoyl chloride, 2,4,6-trifluorophenylcarbamoyl chloride, 3,4,5-trifluorophenylcarbamoyl chloride, 4-chloro-2,4-difluorophenylcarbamoyl chloride, 2,4-dichloro-5-fluoro-4-nitrophenylcarbamoyl chloride, 2,4,5-trifluoro-3-methyl-6-nitrophenylcarbamoyl chloride, 2,3,4,5-tetrafluorophenylcarbamoyl chloride, 2,3,5,6-tetrafluorophenylcarbamoyl chloride, 2,3,5,6-tetrafluoro-4-methylphenylcarbamoyl chloride, 2,3,4,5-tetrafluoro-6-nitrophenylcarbamoyl chloride, 2,3,4,5,6-pentafluorophenylcarbamoyl chloride, 2-(trifluoromethyl)phenylcarbamoyl chloride, 3-(trifluoromethyl)phenylcarbamoyl chloride, 4-(trifluoromethyl)phenylcarbamoyl chloride, 3-trifluoromethyl-4-ethoxyphenylcarbamoyl chloride, 3,5-bis(trifluoromethyl)phenylcarbamoyl chloride, 2,4,6-tris(trifluoromethyl)phenylcarbamoyl chloride, 4-(pentafluoroethyl)phenylcarbamoyl chloride, 4-(3-tetrafluoropropyl)phenylcarbamoyl chloride, 2,3,5,6-tetrafluoro-4-(trifluoromethyl)phenylcarbamoyl chloride, 2,3,5,6-tetrafluoro-4-(trifluorovinyl)phenylcarbamoyl chloride and 2,3,5,6-tetrafluoro-4-(pentafluoroallyl)phenylcarbamoyl chloride.

Examples of compounds of formula (19) in which Z is a group of formula (5) include, but are not limited to, 2-fluorophenylthiocarbamoyl chloride, 3-fluorophenylthiocarbamoyl chloride, 4-fluorophenylthiocarbamoyl chloride, 2-fluoro-4-methylphenylthiocarbamoyl chloride, 2-fluoro-5-methylphenylthiocarbamoyl chloride, 3-fluoro-4-methylphenylthiocarbamoyl chloride, 3-fluoro-6-methylphenylthiocarbamoyl chloride, 4-fluoro-2-methylphenylthiocarbamoyl chloride, 4-fluoro-3-methylphenylthiocarbamoyl chloride, 2,3-difluorophenylthiocarbamoyl chloride, 2,4-difluorophenylthiocarbamoyl chloride, 2,5-difluorophenylthiocarbamoyl chloride, 2,6-difluorophenylthiocarbamoyl chloride, 3,4-difluorophenylthiocarbamoyl chloride, 3,5-difluorophenylthiocarbamoyl chloride, 3-chloro-2-fluorophenylthiocarbamoyl chloride, 4-chloro-2-fluorophenylthiocarbamoyl chloride, 5-chloro-2-fluorophenylthiocarbamoyl chloride, 2-chloro-6-fluorophenylthiocarbamoyl chloride, 2-chloro-3-fluorophenylthiocarbamoyl chloride, 2-chloro-4-fluorophenylthiocarbamoyl chloride, 2-chloro-5-fluorophenylthiocarbamoyl chloride, 3-chloro-4-fluorophenylthiocarbamoyl chloride, 3-chloro-5-fluorophenylthiocarbamoyl chloride, 3-bromo-2-fluorophenylthiocarbamoyl chloride, 4-bromo-2-fluorophenylthiocarbamoyl chloride, 5-bromo-2-fluorophenylthiocarbamoyl chloride, 2-bromo-6-fluorophenylthiocarbamoyl chloride, 2-bromo-3-fluorophenylthiocarbamoyl chloride, 2-bromo-4-fluorophenylthiocarbamoyl chloride, 2-bromo-5-fluorophenylthiocarbamoyl chloride, 3-bromo-4-fluorophenylthiocarbamoyl chloride, 3-bromo-5-fluorophenylthiocarbamoyl chloride, 2-fluoro-5-iodophenylthiocarbamoyl chloride, 2-fluoro-6-iodophenylthiocarbamoyl chloride, 2-fluoro-3-(trifluoromethyl)phenylthiocarbamoyl chloride, 2-fluoro-5-(trifluoromethyl)phenylthiocarbamoyl chloride, 2-fluoro-6-(trifluoromethyl)phenylthiocarbamoyl chloride, 3-fluoro-4-(trifluoromethyl)phenylthiocarbamoyl chloride, 3-fluoro-5-(trifluoromethyl)phenylthiocarbamoyl chloride, 3-fluoro-6-(trifluoromethyl)phenylthiocarbamoyl chloride, 4-fluoro-2-(trifluoromethyl)phenylthiocarbamoyl chloride, 4-fluoro-3-(trifluoromethyl)phenylthiocarbamoyl chloride, 2-fluoro-4-nitrophenylthiocarbamoyl chloride, 2-fluoro-5-nitrophenylthiocarbamoyl chloride, 3-fluoro-2-nitrophenylthiocarbamoyl chloride, 3-fluoro-4-nitrophenylthiocarbamoyl chloride, 3-fluoro-6-nitrophenylthiocarbamoyl chloride, 4-fluoro-2-nitrophenylthiocarbamoyl chloride, 4-fluoro-3-nitrophenylthiocarbamoyl chloride, 4-cyano-2-fluorophenylthiocarbamoyl chloride, 3-cyano-5-fluorophenylthiocarbamoyl chloride, 2,3,4-trifluorophenylthiocarbamoyl chloride, 2,3,5-trifluorophenylthiocarbamoyl chloride, 2,3,6-trifluorophenylthiocarbamoyl chloride, 2,4,5-trifluorophenylthiocarbamoyl chloride, 2,4,6-trifluorophenylthiocarbamoyl chloride, 3,4,5-trifluorophenylthiocarbamoyl chloride, 4-chloro-2,4-difluorophenylthiocarbamoyl chloride, 2,4-dichloro-5- fluoro-4-nitrophenylthiocarbamoyl chloride, 2,4,5-trifluoro-3-methyl-6-nitrophenylthiocarbamoyl chloride, 2,3,4,5-tetrafluorophenylthiocarbamoyl chloride, 2,3,5,6-tetrafluorophenylthiocarbamoyl chloride, 2,3,5,6-tetrafluoro-4-methylphenylthiocarbamoyl chloride, 2,3,4,5-tetrafluoro-6-nitrophenylthiocarbamoyl chloride, 2,3,4,5,6-pentafluorophenylthiocarbamoyl chloride, 2-(trifluoromethyl)phenylthiocarbamoyl chloride, 3-(trifluoromethyl)phenylthiocarbamoyl chloride, 4-(trifluoromethyl)phenylthiocarbamoyl chloride, 3-trifluoromethyl-4-ethoxyphenylthiocarbamoyl chloride, 3,5-bis(trifluoromethyl)phenylthiocarbamoyl chloride, 2,4,6-tris(trifluoromethyl)phenylthiocarbamoyl chloride, 4-(pentafluoroethyl)phenylthiocarbamoyl chloride, 4-(3-tetrafluoropropyl)phenylthiocarbamoyl chloride, 2,3,5,6-tetrafluoro-4-(trifluoromethyl)phenylthiocarbamoyl chloride, 2,3,5,6-tetrafluoro-4-(trifluorovinyl)phenylthiocarbamoyl chloride and 2,3,5,6-tetrafluoro-4-(pentafluoroallyl)phenylthiocarbamoyl chloride.

Examples of compounds of formula (19) in which Z is a group of formula (6) include, but are not limited to, 2-fluorobenzyl chloride, 3-fluorobenzyl chloride, 4-fluorobenzyl chloride, 2-fluoro-4-methylbenzyl chloride, 2-fluoro-5-methylbenzyl chloride, 3-fluoro-4-methylbenzyl chloride, 3-fluoro-6-methylbenzyl chloride, 4-fluoro-2-methylbenzyl chloride, 4-fluoro-3-methylbenzyl chloride, 2,3-difluorobenzyl chloride, 2,4-difluorobenzyl chloride, 2,5-difluorobenzyl chloride, 2,6-difluorobenzyl chloride, 3,4-difluorobenzyl chloride, 3,5-difluorobenzyl chloride, 3-chloro-2-fluorobenzyl chloride, 4-chloro-2-fluorobenzyl chloride, 5-chloro-2-fluorobenzyl chloride, 2-chloro-6-fluorobenzyl chloride, 2-chloro-3-fluorobenzyl chloride, 2-chloro-4-fluorobenzyl chloride, 2-chloro-5-fluorobenzyl chloride, 3-chloro-4-fluorobenzyl chloride, 3-chloro-5-fluorobenzyl chloride, 3-bromo-2-fluorobenzyl chloride, 4-bromo-2-fluorobenzyl chloride, 5-bromo-2-fluorobenzyl chloride, 2-bromo-6-fluorobenzyl chloride, 2-bromo-3-fluorobenzyl chloride, 2-bromo-4-fluorobenzyl chloride, 2-bromo-5-fluorobenzyl chloride, 3-bromo-4-fluorobenzyl chloride, 3-bromo-5-fluorobenzyl chloride, 2-fluoro-5-iodobenzyl chloride, 2-fluoro-6-iodobenzyl chloride, 2-fluoro-3-(trifluoromethyl)benzyl chloride, 2-fluoro-5-(trifluoromethyl)benzyl chloride, 2-fluoro-6-(trifluoromethyl)benzyl chloride, 3-fluoro-4-(trifluoromethyl)benzyl chloride, 3-fluoro-5-(trifluoromethyl)benzyl chloride, 3-fluoro-6-(trifluoromethyl)benzyl chloride, 4-fluoro-2-(trifluoromethyl)benzyl chloride, 4-fluoro-3-(trifluoromethyl)benzyl chloride, 2-fluoro-4-nitrobenzyl chloride, 2-fluoro-5-nitrobenzyl chloride, 3-fluoro-2-nitrobenzyl chloride, 3-fluoro-4-nitrobenzyl chloride, 3-fluoro-6-nitrobenzyl chloride, 4-fluoro-2-nitrobenzyl chloride, 4-fluoro-3-nitrobenzyl chloride, 4-cyano-2-fluorobenzyl chloride, 3-cyano-5-fluorobenzyl chloride, 2,3,4-trifluorobenzyl chloride, 2,3,5-trifluorobenzyl chloride, 2,3,6-trifluorobenzyl chloride, 2,4,5-trifluorobenzyl chloride, 2,4,6-trifluorobenzyl chloride, 3,4,5-trifluorobenzyl chloride, 4-chloro-2,4-difluorobenzyl chloride, 2,4-dichloro-5-fluoro-4-nitrobenzyl chloride, 2,4,5-trifluoro-3-methyl-6-nitrobenzyl chloride, 2,3,4,5-tetrafluorobenzyl chloride, 2,3,5,6-tetrafluorobenzyl chloride, 2,3,5,6-tetrafluoro-4-methylbenzyl chloride, 2,3,4,5-tetrafluoro-6-nitrobenzyl chloride, 2,3,4,5,6-pentafluorobenzyl chloride, 2-(trifluoromethyl)benzyl chloride, 3-(trifluoromethyl)benzyl chloride, 4-(trifluoromethyl)benzyl chloride, 3-trifluoromethyl-4-ethoxybenzyl chloride, 3,5-bis(trifluoromethyl)benzyl chloride, 2,4,6-tris(trifluoromethyl)benzyl chloride, 4-(pentafluoroethyl)benzyl chloride, 4-(3-tetrafluoropropyl)benzyl chloride, 2,3,5,6-tetrafluoro-4-(trifluoromethyl)benzyl chloride, 2,3,5,6-tetrafluoro-4-(trifluorovinyl)benzyl chloride and 2,3,5,6-tetrafluoro-4-(pentafluoroallyl)benzyl chloride.

Examples of compounds of formula (19) in which Z is a group of formula (7) include, but are not limited to, 2-fluorobenzenesulfonyl chloride, 3-fluorobenzenesulfonyl chloride, 4-fluorobenzenesulfonyl chloride, 2-fluoro-4-methylbenzenesulfonyl chloride, 2-fluoro-5-methylbenzenesulfonyl chloride, 3-fluoro-4-methylbenzenesulfonyl chloride, 3-fluoro-6-methylbenzenesulfonyl chloride, 4-fluoro-2-methylbenzenesulfonyl chloride, 4-fluoro-3-methylbenzenesulfonyl chloride, 2,3-difluorobenzenesulfonyl chloride, 2,4-difluorobenzenesulfonyl chloride, 2,5-difluorobenzenesulfonyl chloride, 2,6-difluorobenzenesulfonyl chloride, 3,4-difluorobenzenesulfonyl chloride, 3,5-difluorobenzenesulfonyl chloride, 3-chloro-2-fluorobenzenesulfonyl chloride, 4-chloro-2-fluorobenzenesulfonyl chloride, 5-chloro-2-fluorobenzenesulfonyl chloride, 2-chloro-6-fluorobenzenesulfonyl chloride, 2-chloro-3-fluorobenzenesulfonyl chloride, 2-chloro-4-fluorobenzenesulfonyl chloride, 2-chloro-5-fluorobenzenesulfonyl chloride, 3-chloro-4-fluorobenzenesulfonyl chloride, 3-chloro-5-fluorobenzenesulfonyl chloride, 3-bromo-2-fluorobenzenesulfonyl chloride, 4-bromo-2-fluorobenzenesulfonyl chloride, 5-bromo-2-fluorobenzenesulfonyl chloride, 2-bromo-6-fluorobenzenesulfonyl chloride, 2-bromo-3-fluorobenzenesulfonyl chloride, 2-bromo-4-fluorobenzenesulfonyl chloride, 2-bromo-5-fluorobenzenesulfonyl chloride, 3-bromo-4-fluorobenzenesulfonyl chloride, 3-bromo-5-fluorobenzenesulfonyl chloride, 2-fluoro-5-iodobenzenesulfonyl chloride, 2-fluoro-6-iodobenzenesulfonyl chloride, 2-fluoro-3-(trifluoromethyl)benzenesulfonyl chloride, 2-fluoro-5-(trifluoromethyl)benzenesulfonyl chloride, 2-fluoro-6-(trifluoromethyl)benzenesulfonyl chloride, 3-fluoro-4-(trifluoromethyl)benzenesulfonyl chloride, 3-fluoro-5-(trifluoromethyl)benzenesulfonyl chloride, 3-fluoro-6-(trifluoromethyl)benzenesulfonyl chloride, 4-fluoro-2-(trifluoromethyl)benzenesulfonyl chloride, 4-fluoro-3-(trifluoromethyl)benzenesulfonyl chloride, 2-fluoro-4-nitrobenzenesulfonyl chloride, 2-fluoro-5-nitrobenzenesulfonyl chloride, 3-fluoro-2-nitrobenzenesulfonyl chloride, 3-fluoro-4-nitrobenzenesulfonyl chloride, 3-fluoro-6-nitrobenzenesulfonyl chloride, 4-fluoro-2-nitrobenzenesulfonyl chloride, 4-fluoro-3-nitrobenzenesulfonyl chloride, 4-cyano-2-fluorobenzenesulfonyl chloride, 3-cyano-5-fluorobenzenesulfonyl chloride, 2,3,4-trifluorobenzenesulfonyl chloride, 2,3,5-trifluorobenzenesulfonyl chloride, 2,3,6-trifluorobenzenesulfonyl chloride, 2,4,5-trifluorobenzenesulfonyl chloride, 2,4,6-trifluorobenzenesulfonyl chloride, 3,4,5-trifluorobenzenesulfonyl chloride, 4-chloro-2,4-difluorobenzenesulfonyl chloride, 2,4-dichloro-5-fluoro-4-nitrobenzenesulfonyl chloride, 2,4,5-trifluoro-3-methyl-6-nitrobenzenesulfonyl chloride, 2,3,4,5-tetrafluorobenzenesulfonyl chloride, 2,3,5,6-tetrafluorobenzenesulfonyl chloride, 2,3,5,6-tetrafluoro-4-methylbenzenesulfonyl chloride, 2,3,4,5-tetrafluoro-6-nitrobenzenesulfonyl chloride, 2,3,4,5,6-pentafluorobenzenesulfonyl chloride, 2-(trifluoromethyl)

benzenesulfonyl chloride, 3-(trifluoromethyl)benzenesulfonyl chloride, 4-(trifluoromethyl)benzenesulfonyl chloride, 3-trifluoromethyl-4-ethoxybenzenesulfonyl chloride, 3,5-bis(trifluoromethyl)benzenesulfonyl chloride, 2,4,6-tris(trifluoromethyl)benzenesulfonyl chloride, 4-(pentafluoroethyl) benzenesulfonyl chloride, 4-(3-tetrafluoropropyl) benzenesulfonyl chloride, 2,3,5,6-tetrafluoro-4-(trifluoromethyl)benzenesulfonyl chloride, 2,3,5,6-tetrafluoro-4-(trifluorovinyl)benzenesulfonyl chloride and 2,3,5,6-tetrafluoro-4-(pentafluoroallyl)benzenesulfonyl chloride.

A base may be used in the third step. This base is exemplified by the same bases that may be used in the first step. Of these, owing especially to the ease of handling, preferred examples include triethylamine, pyridine and diisopropylethylamine.

The reaction solvent is preferably an aprotic organic solvent, examples of which include N,N-dimethylformamide, N,N-dimethylacetamide, N-methylpyrrolidone, 1,3-dimethyl-2-imidazolidinone, dimethylsulfoxide, tetrahydrofuran and dioxane. From the standpoint of the ease of removing the reaction solvent following the reaction, N,N-dimethylformamide, N,N-dimethylacetamide, tetrahydrofuran, dioxane, toluene, xylene and mesitylene are preferred.

The charging ratio between the intermediate of formula (18) and the compound of formula (19) is preferably from 2 to 6 equivalents, and more preferably from 2 to 3 equivalents, of the compound of formula (19) with respect to the intermediate of formula (18).

In the third step, the reaction temperature is suitably set within the range of the solvent melting point to the solvent boiling point while taking into account the types and amounts of the starting compounds and catalyst used, and is typically from about 0° C. to about 200° C., and preferably from 0 to 50° C. The reaction time differs according to such factors as the starting compounds used and the reaction temperature, and therefore cannot be strictly specified, but is generally from about 1 hour to about 24 hours.

Following reaction completion, the target fluorine atom-containing compound can be obtained by work-up in the usual manner.

The compound of formula (19) can be obtained by a known method or by acquiring a commercial product.

[Charge-Transporting Substance]

The fluorine atom-containing compound of the invention can be suitably used as a charge-transporting substance, especially a hole-transporting substance. In this invention, "charge-transporting" is synonymous with electrically conductive. As used herein, a "charge-transporting substance" refers to a substance which itself has a charge-transporting ability. Also, a "charge-transporting varnish" may refer to a substance which itself has a charge-transporting ability or a substance from which there can be obtained a solid film that has a charge-transporting ability.

[Charge-Transporting Varnish]

The charge-transporting varnish of the invention includes a charge-transporting substance composed of the fluorine atom-containing compound, and an organic solvent.

[Organic Solvent]

High-solvency solvents that are able to dissolve well the fluorine atom-containing compound may be used as the organic solvent employed when preparing the charge-transporting varnish of the invention.

Examples of such high-solvency solvents include amide solvents such as N,N-dimethylformamide, N,N-dimethylacetamide, N,N-dimethylisobutyramide, N-methylpyrrolidone and 1,3-dimethyl-2-imidazolidinone; chlorinated solvents such as chloroform and chlorobenzene; aromatic hydrocarbon solvents such as toluene, xylene, tetralin, cyclohexylbenzene and 3-phenoxytoluene; ketone solvents such as isophorone and cyclohexanone; ester solvents such as ethyl acetate and methyl benzoate; polyhydric alcohol solvents such as ethylene glycol and diethylene glycol; ether solvents such as tetrahydrofuran, dioxane, anisole and diethylene glycol monomethyl ether; alcohol solvents such as isopropyl alcohol, cyclohexanol and benzyl alcohol; and sulfoxides such as dimethylsulfoxide. These solvents may be used singly, or two or more may be used in admixture. The amount of use thereof may be set to from 5 to 100 wt % of the overall solvent used in the varnish.

The charge-transporting substances are all preferably completely dissolved or uniformly dispersed in the solvent, and are more preferably completely dissolved.

In the invention, the varnish may include at least one high-viscosity organic solvent having a viscosity at 25° C. of from 10 to 200 mPa·s, and especially from 35 to 150 mPa·s, and having a boiling point at normal pressure (atmospheric pressure) of from 50 to 300° C., and especially from 150 to 250° C. By adding such a solvent, adjustment of the varnish viscosity is easy and it is possible to prepare a varnish which reproducibly provides thin films of high flatness and which is suitable for the coating method to be employed.

Examples of high-viscosity organic solvents include, but are not limited to, cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butanediol, propylene glycol and hexylene glycol. Depending on the type of host used, the high-viscosity organic solvent may also serve as a high-solvency solvent.

The ratio in which the high-viscosity organic solvent is added relative to the overall solvent used in the inventive varnish is preferably within a range where solids do not precipitate out. The addition ratio is preferably from 5 to 90 wt %, provided that solids do not precipitate out.

In addition, other solvents may be admixed in a proportion, based on the overall solvent used in the varnish, of from 1 to 90 wt %, and preferably from 1 to 50 wt %, for such purposes as to increase the wettability on a substrate, adjust the surface tension of the solvent, adjust the polarity and adjust the boiling point.

Examples of such solvents include, but are not limited to, propylene glycol monomethyl ether, ethylene glycol monobutyl ether, diethylene glycol diethyl ether, diethylene glycol monomethyl ether, diethylene glycol dimethyl ether, diethylene glycol monoethyl ether acetate, diethylene glycol monobutyl ether acetate, dipropylene glycol monomethyl ether, propylene glycol monomethyl ether acetate, diethylene glycol monoethyl ether, diacetone alcohol, γ-butyrolactone, ethyl lactate and n-hexyl acetate. These solvents may be used singly, or two or more may be used in admixture. Depending on the type of host, these solvents may also serve as a high-solvency solvent.

In this invention, to reproducibly obtain thin films of a higher flatness, it is desirable for the charge-transporting varnish, following dissolution of the charge-transporting substance in an organic solvent, to be filtered using a submicron-order filter or the like.

To ensure a sufficient film thickness while suppressing precipitation of the charge-transporting substance, the solids concentration in the inventive varnish is typically from about 0.1 wt % to about 20 wt %, and preferably from 0.5 to 10 wt %. As used herein, "solids" refers to the ingredients that remain when the solvent is removed from the ingredients included in the varnish. The viscosity of the inventive varnish at 25° C. is typically from 1 to 50 mPa·s.

[Fluorine Atom-Free Charge-Transporting Substance]

The charge-transporting varnish of the invention may further include a charge-transporting substance which contains no fluorine atoms. The fluorine atom-free charge-transporting substances is exemplified by charge-transporting oligomers such as aniline derivatives, thiophene derivatives and pyrrole derivatives. The molecular weight of this fluorine atom-free charge-transporting oligomer is typically from 200 to 8,000. However, from the standpoint of preparing a varnish that provides thin films having a high charge-transporting ability, the molecular weight is preferably at least 300, more preferably at least 400, and even more preferably at least 500. From the standpoint of preparing a uniform varnish that provides thin films of a high flatness, the molecular weight is preferably not more than 6,000, more preferably not more than 5,000, even more preferably not more than 4,000, and still more preferably not more than 3,000.

Of such fluorine atom-free charge-transporting oligomers, from the standpoint of the balance between the solubility in organic solvents and the charge-transporting ability of the resulting thin film, aniline derivatives are preferred. Exemplary aniline derivatives include the oligoaniline derivatives mentioned in JP-A 2002-151272, the oligoaniline compounds mentioned in WO 2004/105446, the oligoaniline compounds mentioned in WO 2008/032617, the oligoaniline compounds mentioned in 2008/032616 and the aryldiamine compounds mentioned in WO 2013/042623.

Suitable use can also be made of aniline derivatives of formula (20) below.

propynyl, n-2-propynyl, n-1-butynyl, n-2-butynyl, n-3-butynyl, 1-methyl-2-propynyl, n-1-pentynyl, n-2-pentynyl, n-3-pentynyl, n-4-pentynyl, 1-methyl-n-butynyl, 2-methyl-n-butynyl, 3-methyl-n-butynyl, 1,1-dimethyl-n-propynyl, n-1-hexynyl, n-1-decynyl, n-1-pentadecynyl and n-1-eicosynyl groups.

Specific examples of the heteroaryl group of 2 to 20 carbon atoms include 2-thienyl, 3-thienyl, 2-furanyl, 3-furanyl, 2-oxazolyl, 4-oxazolyl, 5-oxazolyl, 3-isooxazolyl, 4-isooxazolyl, 5-isooxazolyl, 2-thiazolyl, 4-thiazolyl, 5-thiazolyl, 3-isothiazolyl, 4-isothiazolyl, 5-isothiazolyl, 2-imidazolyl, 4-imidazolyl, 2-pyridyl, 3-pyridyl and 4-pyridyl groups.

$R^{107}$ and $R^{108}$ are each independently a hydrogen atom, a chlorine atom, a bromine atom, an iodine atom, a nitro group, a cyano group, an amino group, an aldehyde group, a hydroxyl group, a thiol group, a sulfonic acid group, a carboxyl group, an alkyl group of 1 to 20 carbon atoms, alkenyl group of 2 to 20 carbon atoms or alkynyl group of 2 to 20 carbon atoms which may be substituted with $Z^{11}$, an aryl group of 6 to 20 carbon atoms or heteroaryl group of 2 to 20 carbon atoms which may be substituted with $Z^{12}$, or —NHY$^2$, —NY$^3$Y$^4$, —C(O)Y$^5$, —OY$^6$, —SY$^7$, —SO$_3$Y$^8$, —C(O)OY$^9$, —OC(O)Y$^{10}$, —C(O)NHY$^{11}$ or —C(O)NY$^{12}$Y$^{13}$.

$Y^2$ to $Y^{13}$ are each independently an alkyl group of 1 to 20 carbon atoms, alkenyl group of 2 to 20 carbon atoms or alkynyl group of 2 to 20 carbon atoms which may be substituted with $Z^{11}$, or an aryl group of 6 to 20 carbon atoms or heteroaryl group of 2 to 20 carbon atoms which may be substituted with $Z^{12}$.

[Chem. 22]

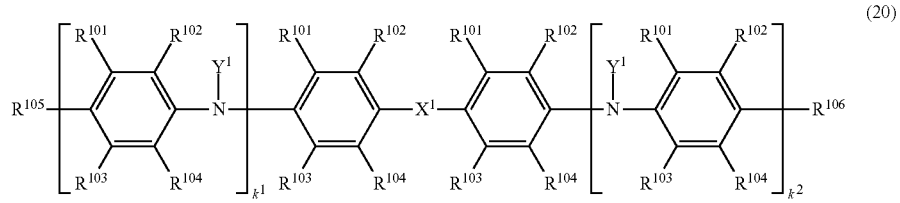

In formula (20), $X^1$ represents —NY$^1$—, —O—, —S—, —(CR$^{107}$R$^{108}$)$_L$— or a single bond. When k$^1$ or k$^2$ is 0, $X^1$ represents —NY$^1$—.

Each $Y^1$ is independently a hydrogen atom, an alkyl group of 1 to 20 carbon atoms, alkenyl group of 2 to 20 carbon atoms or alkynyl group of 2 to 20 carbon atoms which may be substituted with $Z^{11}$, or an aryl group of 6 to 20 carbon atoms or heteroaryl group of 2 to 20 carbon atoms which may be substituted with $Z^{12}$.

The alkyl groups of 1 to 20 carbon atoms and aryl groups of 6 to 20 carbon atoms are exemplified in the same way as mentioned above.

The alkenyl group of 2 to 20 carbon atoms may be linear, branched or cyclic. Specific examples include ethenyl, n-1-propenyl, n-2-propenyl, 1-methylethenyl, n-1-butenyl, n-2-butenyl, n-3-butenyl, 2-methyl-1-propenyl, 2-methyl-2-propenyl, 1-ethylethenyl, 1-methyl-1-propenyl, 1-methyl-2-propenyl, n-1-pentenyl, n-1-decenyl and n-1-eicosenyl groups.

The alkynyl group of 2 to 20 carbon atoms may be linear, branched or cyclic. Specific examples include ethynyl, n-1-

$Z^{11}$ is a chlorine atom, a bromine atom, an iodine atom, a nitro group, a cyano group, an amino group, an aldehyde group, a hydroxyl group, a thiol group, a sulfonic acid group, a carboxyl group, or an aryl group of 6 to 20 carbon atoms or heteroaryl group of 2 to 20 carbon atoms which may be substituted with $Z^{13}$.

$Z^{12}$ is a chlorine atom, a bromine atom, an iodine atom, a nitro group, a cyano group, an amino group, an aldehyde group, a hydroxyl group, a thiol group, a sulfonic acid group, a carboxyl group, or an alkyl group of 1 to 20 carbon atoms, alkenyl group of 2 to 20 carbon atoms or alkynyl group of 2 to 20 carbon atoms which may be substituted with $Z^{13}$.

$Z^{13}$ is a chlorine atom, a bromine atom, an iodine atom, a nitro group, a cyano group, an amino group, an aldehyde group, a hydroxyl group, a thiol group, a sulfonic acid group or a carboxyl group.

The alkyl, alkenyl, alkynyl, aryl and heteroaryl groups on $R^{107}$, $R^{108}$ and $Y^2$ to $Y^{13}$ are exemplified in the same way as described above.

Of these, $R^{107}$ and $R^{108}$ are preferably hydrogen atoms or alkyl groups of 1 to 20 carbon atoms which may be substituted with $Z^{11}$, more preferably hydrogen atoms or methyl groups which may be substituted with $Z^{11}$, and most preferably both hydrogen atoms.

L, which represents the number of divalent groups of the formula —($CR^{107}R^{108}$)—, is an integer from 1 to 20, preferably from 1 to 10, more preferably from 1 to 5, even more preferably 1 or 2, and most preferably 1. When L is 2 or more, the plurality of $R^{107}$ groups may be mutually the same or different, and the plurality of $R^{108}$ may be mutually the same or different.

In particular, $X^1$ is preferably —$NY^1$— or a single bond. $Y^1$ is preferably a hydrogen atom or an alkyl group of 1 to 20 carbon atoms which may be substituted with $Z^{11}$, more preferably a hydrogen atom or a methyl group which may be substituted with $Z^{11}$, and most preferably a hydrogen atom.

In formula (20), $R^{101}$ to $R^{106}$ are each independently a hydrogen atom, a chlorine atom, a bromine atom, an iodine atom, a nitro group, a cyano group, an amino group, an aldehyde group, a hydroxyl group, a thiol group, a sulfonic acid group, a carboxyl group, an alkyl group of 1 to 20 carbon atoms, alkenyl group of 2 to 20 carbon atoms or alkynyl group of 2 to 20 carbon atoms which may be substituted with $Z^{11}$, an aryl group of 6 to 20 carbon atoms or heteroaryl group of 2 to 20 carbon atoms which may be substituted with $Z^{12}$, or —$NHY^2$, —$NY^3Y^4$, —$C(O)Y^5$, —$OY^6$, —$SY^7$, —$SO_3Y^8$, —$C(O)OY^9$, —$OC(O)Y^{10}$, —$C(O)NHY^{11}$ or —$C(O)NY^{12}Y^{13}$ (wherein $Y^2$ to $Y^{13}$ are as defined above). These alkyl, alkenyl, alkynyl, aryl and heteroaryl groups are exemplified in the same way as above.

In particular, in formula (20), $R^{101}$ to $R^{104}$ are each preferably a hydrogen atom, a halogen atom, an alkyl group of 1 to 10 carbon atoms which may be substituted with $Z^{11}$, or an aryl group of 6 to 14 carbon atoms which may be substituted with $Z^{12}$; more preferably a hydrogen atom or an alkyl group of 1 to 10 carbon atoms; and most preferably a hydrogen atom.

$R^{105}$ and $R^{106}$ are each preferably a hydrogen atom, a chlorine atom, a bromine atom, an iodine atom, an alkyl group of 1 to 10 carbon atoms which may be substituted with $Z^{11}$, an aryl group of 6 to 14 carbon atoms which may be substituted with $Z^{12}$, or a diphenylamino group which may be substituted with $Z^{12}$ (the phenyl group —$NY^3Y^4$ wherein $Y^3$ and $Y^4$ may be substituted with $Z^{12}$); more preferably a hydrogen atom or a diphenylamino group; and even more preferably both hydrogen atoms or both diphenylamino groups.

Of these, a combination in which $R^{101}$ to $R^{104}$ are each preferably a hydrogen atom or an alkyl group of 1 to 10 carbon atoms, $R^{105}$ and $R^{106}$ are each a hydrogen atom or a diphenylamino group, $X^1$ is —$NY^1$— or a single bond and $Y^1$ is a hydrogen atom or a methyl group is preferred; and a combination in which $R^{101}$ to $R^{104}$ are each a hydrogen atom, $R^{105}$ and $R^{106}$ are both hydrogen atoms or diphenylamino groups, and $X^1$ is —NH— or a single bond is more preferred.

In formula (20), $k^1$ and $k^2$ are each independently an integer of 0 or more and together satisfy the condition $1 \leq k^1+k^2 \leq 20$. Taking into account the balance between the charge transportability of the resulting thin film and the solubility of the aniline derivative, they preferably satisfy the condition $2 \leq k^1+k^2 \leq 8$, more preferably satisfy the condition $2 \leq k^1+k^2 \leq 6$, and even more preferably satisfy the condition $2 \leq k^1+k^2 \leq 4$.

In $Y^1$ to $Y^{13}$ and $R^{101}$ to $R^{108}$, is preferably a chlorine atom, a bromine atom, an iodine atom or an aryl group of 6 to 20 carbon atoms which may be substituted with $Z^{13}$; more preferably a chlorine atom, a bromine atom, an iodine atom or a phenyl group which may be substituted with $Z^{13}$; and most preferably does not exist (i.e., is non-substituting).

$Z^{12}$ is preferably a chlorine atom, a bromine atom, an iodine atom or an alkyl group of 1 to 20 carbon atoms which may be substituted with $Z^{13}$, more preferably a chlorine atom, a bromine atom, an iodine atom or an alkyl group of 1 to 4 carbon atoms which may be substituted with $Z^{13}$; and most preferably does not exist (i.e., is non-substituting).

$Z^{13}$ is preferably a chlorine atom, a bromine atom or an iodine atom; and most preferably does not exist (i.e., is non-substituting).

In $Y^1$ to $Y^{13}$ and $R^{101}$ to $R^{108}$, the number of carbon atoms on the alkyl, alkenyl and alkynyl groups is preferably 10 or less, more preferably 6 or less, and even more preferably 4 or less. The number of carbon atoms on the aryl and heteroaryl groups is preferably 14 or less, more preferably 10 or less, and even more preferably 6 or less.

The method of synthesizing the aniline derivative is exemplified by, without particular limitation, the methods mentioned in *Bulletin of Chemical Society of Japan*, 67, pp. 1749-1752 (1994); *Synthetic Metals*, 84, pp. 119-120 (1997); *Thin Solid Films*, 520(24), pp. 7157-7163 (2012); and WO 2008/032617, WO 2008/032616, WO 2008/129947 and WO 2013/084664.

Specific examples of the aniline derivative of formula (20) include, but are not limited to, those of the following formulas. In the formulas below, "DPA" stands for a diphenylamino group, "Ph" stands for a phenyl group, and "TPA" stands for a p-(diphenylamino)phenyl group.

[Chem. 23]

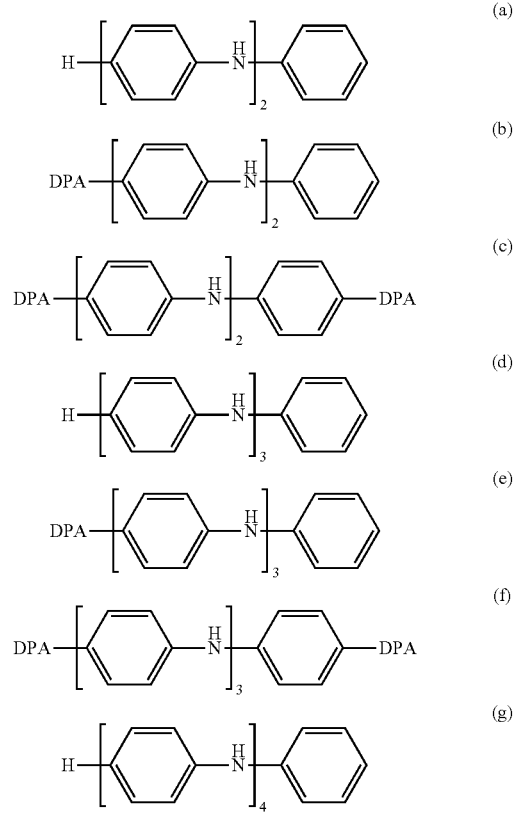

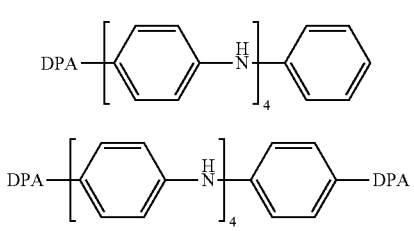

(h)

(i)

[Chem. 24]

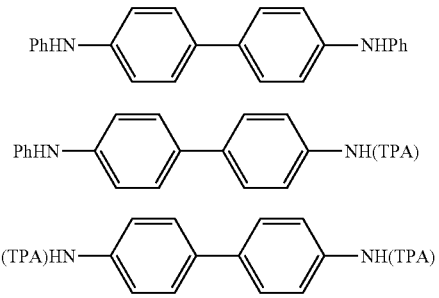

(j)

(k)

(l)

[Dopant]

Depending on the intended use of thin films obtained therefrom, the charge-transporting varnish of the invention may include a dopant for the purpose of, e.g., increasing the charge-transporting performance. The dopant is not particularly limited, so long as it is one that dissolves in at least one of the solvents used in the varnish. Both inorganic dopants and organic dopants may be used. The inorganic and organic dopants may be of one type used alone, or two or more may be used in combination.

When a dopant is included in the charge-transporting varnish of the invention, the content thereof, expressed as a molar ratio with respect to the charge-transporting substance, is preferably from about 0.01 to about 20.0, and more preferably from about 0.4 to about 5.0.

Specific examples of inorganic dopants include inorganic acids such as hydrogen chloride, sulfuric acid, nitric acid and phosphoric acid; metal halides such as aluminum(III) chloride ($AlCl_3$), titanium(IV) tetrachloride ($TiCl_4$), boron tribromide ($BBr_3$), a boron trifluoride-ether complex ($BF_3 \cdot OEt_2$), iron(III) chloride ($FeCl_3$), copper(II) chloride ($CuCl_2$), antimony(V) pentachloride ($SbCl_5$), antimony(V) pentafluoride ($SbF_5$), arsenic(V) pentafluoride ($AsF_5$), phosphorus pentafluoride ($PF_5$) and tris(4-bromophenyl)aluminum hexachloroantimonate (TBPAH); halogens such as $Cl_2$, $Br_2$, $I_2$, ICl, $ICl_3$, IBr and $IF_4$; and heteropolyacids such as phosphomolybdic acid and phosphotungstic acid. Of these, heteropolyacids such as phosphomolybdic acid and phosphotungstic acid are preferred.

Specific examples of organic dopants include the following arylsulfone compounds: benzenesulfonic acid, tosylic acid, p-styrenesulfonic acid, 2-naphthalenesulfonic acid, 4-hydroxybenzenesulfonic acid, 5-sulfosalicylic acid, p-dodecylbenzenesulfonic acid, dihexylbenzenesulfonic acid, 2,5-dihexylbenzenesulfonic acid, dibutylnaphthalenesulfonic acid, 6,7-dibutyl-2-naphthalenesulfonic acid, dodecylnaphthalenesulfonic acid, 3-dodecyl-2-naphthalenesulfonic acid, hexylnaphthalenesulfonic acid, 4-hexyl-1-naphthalenesulfonic acid, octylnaphthalenesulfonic acid, 2-octyl-1-naphthalenesulfonic acid, hexylnaphthalenesulfonic acid, 7-hexyl-1-naphthalenesulfonic acid, 6-hexyl-2-naphthalenesulfonic acid, dinonylnaphthalenesulfonic acid, 2,7-dinonyl-4-naphthalenesulfonic acid, dinonylnaphthalenedisulfonic acid, 2,7-dinonyl-4,5-naphthalenedisulfonic acid, the 1,4-benzodioxanedisulfonic acid compounds mentioned in WO 2005/000832, the arylsulfonic acid compounds mentioned in WO 2006/025342, the arylsulfonic acid compounds mentioned in WO 2009/096352, and polystyrenesulfonic acid.

Arylsulfonic acid compounds of formula (21) or (22) below may also be advantageously used as dopants.

[Chem. 25]

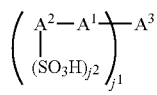 (21)

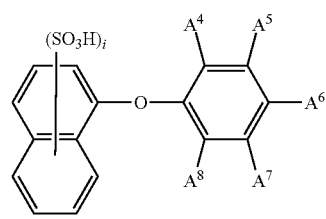 (22)

In formula (21), $A^1$ is —O— or —S—, and is preferably —O—. $A^2$ is preferably a naphthalene ring or an anthracene ring, with a naphthalene ring being preferred. $A^3$ is a divalent to tetravalent perfluorobiphenyl group, and the subscript $j^1$, which represents the number of bonds between $A^1$ and $A^3$, is an integer that satisfies the condition $2 \leq j^1 \leq 4$. It is preferable for $A^3$ to be a divalent perfluorobiphenyl group and for $j^1$ to be 2. The subscript $j^2$, which represents the number of sulfonic acid groups bonded to $A^2$, is an integer that satisfies the condition $1 \leq j^2 \leq 4$, and is preferably 2.

In formula (22), $A^4$ to $A^8$ are each independently a hydrogen atom, a halogen atom, a cyano group, an alkyl group of 1 to 20 carbon atoms, a halogenated alkyl group of 1 to 20 carbon atoms or a halogenated alkenyl group of 2 to 20 carbon atoms, with at least three of $A^4$ to $A^8$ being halogen atoms. The subscript i, which represents the number of sulfonic acid groups bonded to the naphthalene ring, is an integer that satisfies the condition $1 \leq i \leq 4$, and is preferably from 2 to 4, and more preferably 2.

Examples of halogenated alkyl groups of 1 to 20 carbon atoms include trifluoromethyl, 2,2,2-trifluoethyl, perfluoroethyl, 3,3,3-trifluoropropyl, 2,2,3,3,3-pentafluoropropyl, perfluoropropyl, 4,4,4-trifluorobutyl, 3,3,4,4,4-pentafluorobutyl, 2,2,3,3,4,4,4-heptafluorobutyl and perfluorobutyl groups. Examples of halogenated alkenyl groups of 2 to 20 carbon atoms include perfluoroethenyl, 1-perfluoropropenyl, perfluoroallyl and perfluorobutenyl groups.

The halogen atom and the alkyl group of 1 to 20 carbon atoms are exemplified in the same way as above, with the halogen atom preferably being a fluorine atom.

Of these, $A^4$ to $A^8$ are preferably hydrogen atoms, halogen atoms, cyano groups, alkyl groups of 1 to 10 carbon atoms, halogenated alkyl groups of 1 to 10 carbon atoms or halogenated alkenyl groups of 2 to 10 carbon atoms, with at least three of $A^4$ to $A^8$ being fluorine atoms; more preferably hydrogen atoms, fluorine atoms, cyano groups, alkyl groups of 1 to 5 carbon atoms, fluorinated alkyl groups of 1 to 5 carbon atoms or fluorinated alkenyl groups of 2 to 5 carbon atoms, with at least three of $A^4$ to $A^8$ being fluorine atoms; and even more preferably hydrogen atoms, fluorine atoms, cyano groups, perfluoroalkyl groups of 1 to 5 carbon atoms or perfluoroalkenyl groups of 1 to 5 carbon atoms, with $A^4$, $A^5$ and $A^8$ being fluorine atoms.

Here, "perfluoroalkyl group" refers to a group in which all the hydrogen atoms on an alkyl group are substituted with fluorine atoms, and "perfluoroalkenyl group" refers to a group in which all the hydrogen atoms on an alkenyl group are substituted with fluorine atoms.

Arylsulfonic acid compounds of formula (23) below also can be suitably used as dopants.

[Chem. 26]

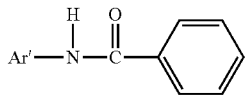

(23)

In the formula, Ar' is a group of formula (24) or (25)

[Chem. 27]

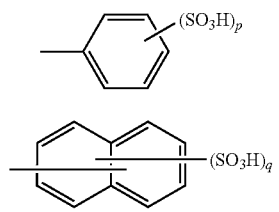

(24)

(25)

(wherein p is an integer from 1 to 5, and q is an integer from 1 to 7).

The arylsulfonic acid compound of formula (23) can be obtained by reacting an amine compound of formula (26) with an acid halide of formula (27) to form an arylsulfonic acid salt of formula (23'), and then subjecting this salt to ion exchange treatment.

[Chem. 28]

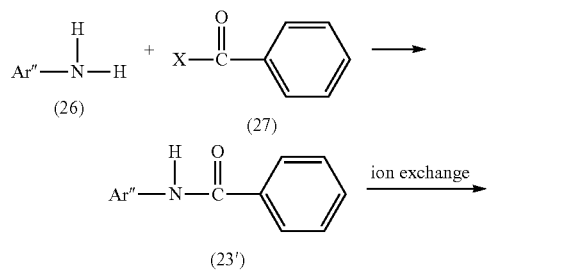

In these formulas, Ar' and X are the same as above, and Ar" represents a group of formula (24') or (25')

[Chem. 29]

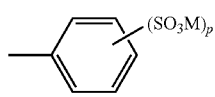

(24')

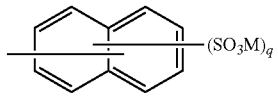

(25')

(wherein p and q are the same as above, and M is an alkali metal atom such as sodium or potassium).

Examples of the amine compound of formula (26) include, but are not limited to, disodium aniline-2,4-disulfonate, disodium aniline-2,5-disulfonate, disodium 8-aminonaphthalene-1,5-disulfonate, disodium 2-aminonaphthalene-1,5-disulfonate, disodium 2-aminonaphthalene-3,6-disulfonate, disodium 7-aminonaphthalene-1,5-disulfonate, disodium 7-aminonaphthalene-2,4-disulfonate and disodium 7-aminonaphthalene-1,3-disulfonate. A hydrate may be used as the amine compound of formula (26).

Examples of the acid halide of formula (27) include benzoyl chloride and benzoyl bromide.

The reaction solvent is preferably an aprotic polar organic solvent, examples of which include N,N-dimethylformamide, N,N-dimethylacetamide, N-methylpyrrolidone, 1,3-dimethyl-2-imidazolidinone, dimethylsulfoxide, tetrahydrofuran and dioxane. From the standpoint of the ease of removing the reaction solvent following the reaction, N,N-dimethylformamide, N,N-dimethylacetamide, tetrahydrofuran and dioxane are preferred.

The reaction temperature may be generally from −50° C. to the boiling point of the solvent used, although the range of 0° C. to 140° C. is preferred. The reaction time is generally from 0.1 to 100 hours.

Following reaction completion, the arylsulfonic acid salt of formula (23') is recovered by filtration, distilling off the reaction solvent or the like, following which the arylsulfonic acid compound of formula (23) can be prepared by protonation of the sulfonic acid salt with a cation-exchange resin.

The acid halide of formula (27) can be obtained by reacting benzoic acid with, for example, an electrophilic halide such as thionyl chloride, oxalyl chloride, phosphoryl chloride, sulfuryl chloride, phosphorus trichloride or phosphorus pentachloride.

Examples of preferred dopants include, but are not limited to, phosphomolybdic acid, phosphotungstic acid and the compounds shown below.

[Chem. 30]

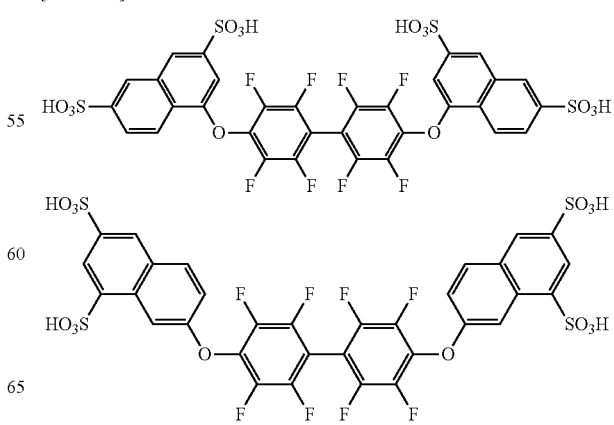

-continued

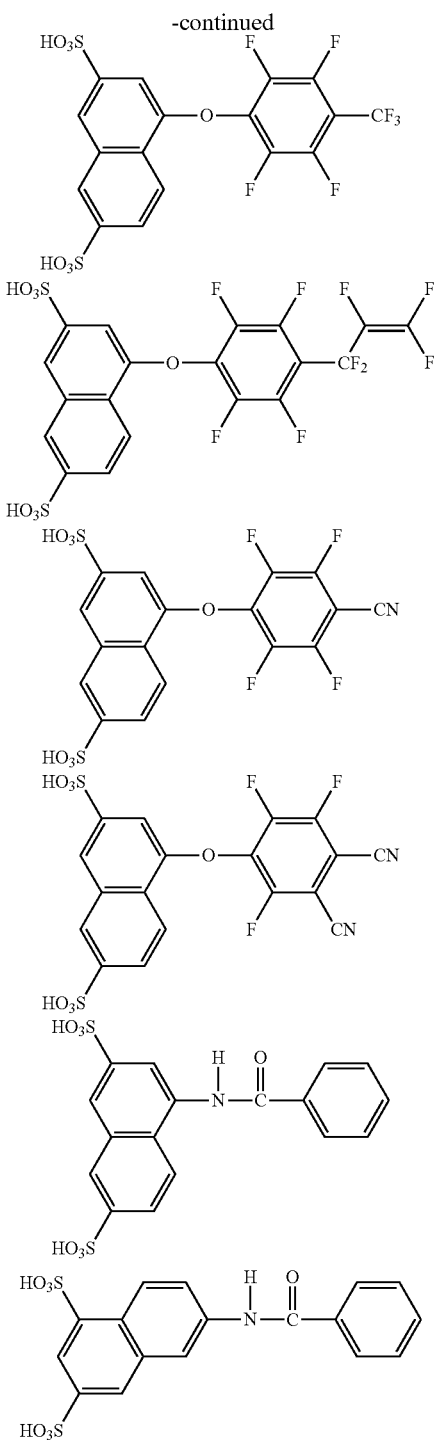

The high-solvency solvent used in the varnish containing the fluorine atom-containing compound, the fluorine atom-free charge-transporting substance and the dopant is exemplified by, but not limited to, organic solvents such as cyclohexanone, N,N-dimethylformamide, N,N-dimethylacetamide, N,N-dimethylisobutyramide, N-methylpyrrolidone and 1,3-dimethyl-2-imidazolidinone. As with charge-transporting varnishes obtained using only a fluorine atom-containing compound, the above-described high-viscosity organic solvents and other solvents may be included when preparing the varnish. The types of such solvents are the same as mentioned above.

The method of preparing the charge-transporting varnish is exemplified by, but not particularly limited to, a method in which the fluorine atom-containing compound of the invention, a fluorine atom-free charge-transporting substance, a dopant and the like are dissolved in a high-solvency solvent, and a high-viscosity organic solvent is added thereto; and a method in which a high-solvency solvent and a high-viscosity organic solvent are mixed together, and the fluorine atom-containing compound of the invention, a fluorine atom-free charge-transporting substance, a dopant and the like are dissolved therein.

[Charge-Transporting Thin Film]

A charge-transporting thin film can be formed on a substrate by coating the charge-transporting varnish of the invention onto the substrate and drying the applied varnish.

Examples of the varnish coating method include, but are not limited to, dipping, spin coating, transfer printing, roll coating, brush coating, inkjet coating, spraying and slit coating. It is preferable for the viscosity and surface tension of the varnish to be adjusted according to the coating method.

When using the varnish of the invention, the liquid film drying conditions are not particularly limited; one example is heating and baking on a hot plate. A dry film can be obtained by heating and baking in a temperature range of generally from about 100° C. to about 260° C. for a period of from about 1 minute to about 1 hour. The baking atmosphere also is not particularly limited.

The thickness of the charge-transporting thin film is not particularly limited. However, when the thin film is to be used as a functional layer in an organic EL device, a film thickness of from 5 to 200 nm is preferred. Methods for changing the film thickness include, for example, changing the solids concentration in the varnish and changing the amount of solution on the substrate during coating.

[Organic EL Device]

Organic EL devices that use the charge-transporting thin film of the invention have a pair of electrodes, an organic layer that functions as a light-emitting layer between these electrodes, and the charge-transporting thin film of the invention between the anode and the light-emitting layer. The device configuration of the organic EL device is exemplified by, but not limited to, anode/hole-injecting layer/hole-transporting layer/electron-blocking layer/light-emitting layer/hole-blocking layer/electron-transporting layer/electron-injecting layer/cathode.

The charge-transporting thin film of the invention can be preferably used as a hole-injecting layer, a hole-transporting layer or a hole-injecting-and-transporting layer in an organic EL device, and can be more preferably used as a hole-transporting layer. As used herein, "hole-injecting layer," "hole-transporting layer" and "hole-injecting-and-transporting layer" refer to layers which are formed between the light-emitting layer and the anode and which have the function of transporting holes from the anode to the light-emitting layer. When only one layer of hole-transporting material is provided between the light-emitting layer and the anode, this is a "hole-injecting-and-transporting layer"; when two or more layers of hole-transporting material are provided between the light-emitting layer and the anode, the layer that is closer to the anode is a "hole-injecting layer" and the other layer is a "hole-transporting layer." In particular, a thin film having not only an ability to receive holes from the anode but also an excellent ability to inject holes into the hole-transporting layer or the light-emitting layer may be used as, respectively, a hole-injecting layer or a hole-injecting-and-transporting layer.

The materials used when fabricating an organic EL device using the charge-transporting varnish of the invention are not particularly limited, and may be suitably selected from among various materials known to the art. The method of fabricating the organic EL device also is not particularly limited.

EXAMPLES

Synthesis Examples, Working Examples and Comparative Examples are given below to more concretely illustrate the invention, although the invention is not limited by these Examples. The equipment used was as follows.
(1) $^1$H-NMR Measurement: 400NB NMR system, from Varian, Inc.; Ascend 500, from BRUKER
(2) Substrate Cleaning: Substrate cleaning machine (reduced-pressure plasma system), from Choshu Industry Co., Ltd.
(3) Varnish Coating: MS-A100 Spin Coater, from Mikasa Co., Ltd.
(4) Film Thickness Measurement: Surfcorder ET-4000 microfigure measuring instrument, from Kosaka Laboratory, Ltd.
(5) Device Fabrication: C-E2L1G1-N Multifunction Vapor Deposition System, from Choshu Industry Co., Ltd.
(6) Measurement of Device Current Density: I-V-L Measurement System from Tech World, Inc.

[1] Synthesis of Compounds

Synthesis Example 1

Synthesis of Intermediate A

[Chem. 31]

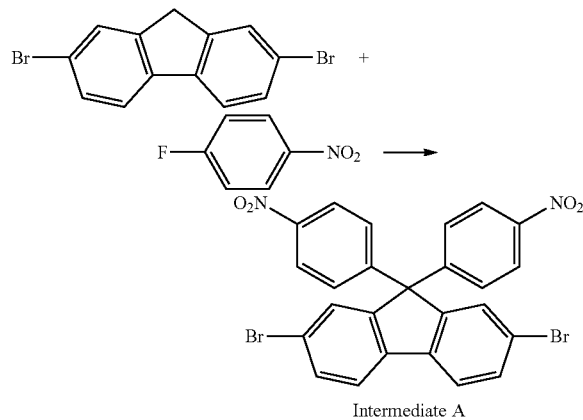

Synthesis was carried out in accordance with the method of *J Mater Chem. C,* 2014, pp. 1068-1075, giving Intermediate A (2,7-dibromo-9,9-bis(4-nitrophenyl)-9H-fluorene).

Working Example 1

Synthesis of Fluorine Atom-Containing Compound A

Working Example 1-1

Synthesis of Intermediate B

[Chem. 32]

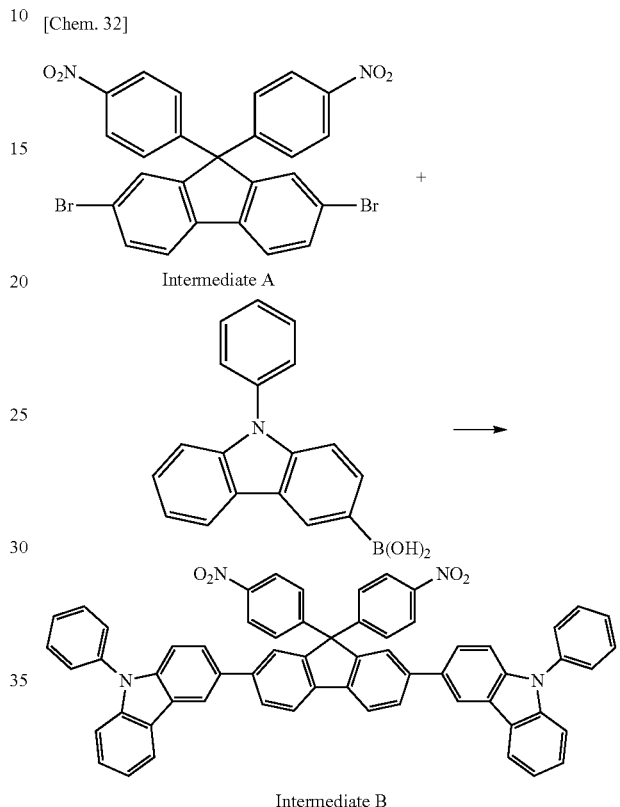

A reactor was charged with 1.80 g of Intermediate A, 2.28 g of (9-phenyl-9H-carbazol-3-yl)boronic acid, 0.18 g of tetrakistriphenylphosphine palladium, 0.30 g of trioctylmethylammonium chloride (Aliquat 336), 18 mL of tetrahydrofuran and 12 mL of a 2 mol/L aqueous solution of potassium carbonate. The reactor was flushed with nitrogen, after which the reactor contents were stirred for 4.5 hours at 60° C. The reaction mixture was returned to room temperature, following which toluene and saturated saline water were added and liquid separation was carried out. The solvent in the resulting organic layer was driven off under reduced pressure. The concentration residue was purified by column chromatography (chloroform/n-hexane, 7/30→90/10), the fractions containing the target substance were collected, and the solvent was driven off under reduced pressure. The concentration residue was dissolved in chloroform, the solution was then added dropwise to n-hexane, and the resulting suspension was filtered. The filtered matter was dried, giving 2.44 g (yield, 86%) of the target substance Intermediate B (3,3'-(9,9-bis(4-nitrophenyl)-9H-fluoren-2,7-diyl)bis(9-phenyl-9H-carbazole)). The $^1$H-NMR measurement results are shown below.

$^1$H-NMR (400 MHz, DMSO-d6) δ [ppm]:
8.76 (d, J=1.6 Hz, 2H), 8.32 (d, J=7.6 Hz, 2H), 8.18-8.20 (m, 4H),
8.14 (d, J=8.0 Hz, 2H), 7.89-7.94 (m, 4H), 7.59-7.74 (m, 14H),
7.52 (t, J=7.2 Hz, 2H), 7.35-7.44 (m, 6H), 7.28 (t, J=8.0 Hz, 2H).

Working Example 1-2

Synthesis of Intermediate C

[Chem. 33]

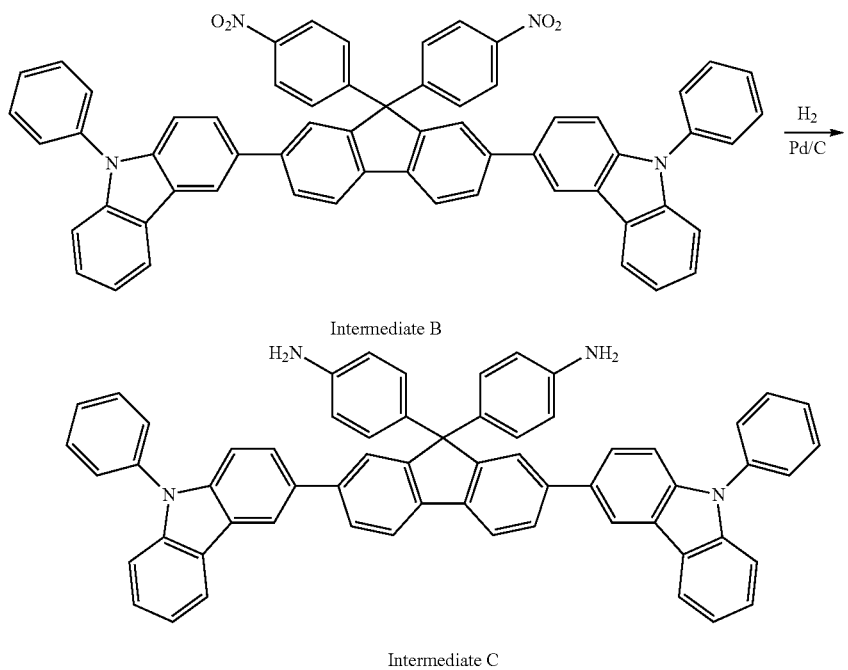

A reactor was charged with 1.80 g of Intermediate B, 0.18 g of 5% palladium on carbon (AER type, from N.E. Chemcat Corporation; containing 49% water) and 18 mL of tetrahydrofuran. The reactor was flushed with nitrogen, after which the reactor contents were stirred for 23 hours at 50° C. The reaction mixture was returned to room temperature, following which tetrahydrofuran was added and filtration was carried out. The filtrate was concentrated, the concentrate was added dropwise to n-hexane, and the suspension was stirred at room temperature, following which filtration was carried out. The filtered matter was dried, giving 1.59 g of a mixture containing the target substance Intermediate C (4,4'-(2,7-bis(9-phenyl-9H-carbazol-3-yl)-9H-fluoren-9,9-diyl)dianiline). Further purification was not carried out, and this mixture was used as the feedstock for the next step.

Working Example 1-3

Synthesis of Fluorine Atom-Containing Compound A

[Chem. 34]

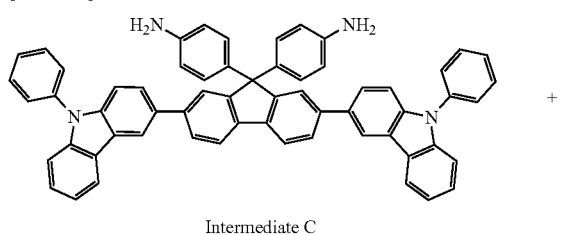

+

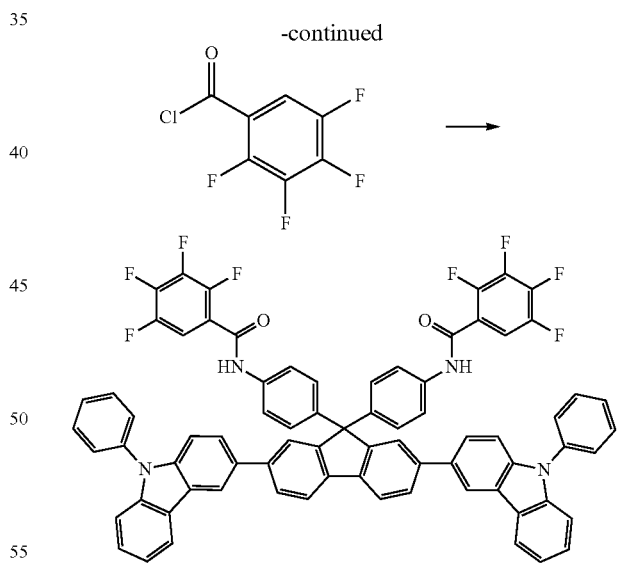

Fluorine Atom-Containing Compound A

A reactor was charged with 1.00 g of the above Intermediate C-containing mixture, 10 mL of N,N-dimethylformamide and 580 μL of trimethylamine. The reactor was flushed with nitrogen, after which 0.96 g of 2,3,4,5-tetrafluorobenzoyl chloride was added dropwise under cooling in an ice bath. Following the completion of dropwise addition, the system was stirred at room temperature for 3 hours. The reaction mixture was added dropwise to deionized water, following which the system was stirred in this state for 0.5 hour at room temperature. The resulting suspension was filtered, following which the filtered matter was suspended in 2-propanol and filtration was carried out. The filtered matter was dissolved in chloroform, the solution was added dropwise to methanol, and the resulting suspension was stirred at room temperature. Filtration was then carried out and the filtered matter thus obtained was dried, giving 1.02 g (yield, 72%) of the target substance Fluorine Atom-Containing Compound A (N,N'-((2,7-bis(9-phenyl-9H-carbazol-3-yl)-9H-fluoren-9,9-diyl)bis(4,1-phenylene)) bis(2,3,4,5-tetrafluorobenzamide)). The $^1$H-NMR measurement results are shown below.

$^1$H-NMR (400 MHz, DMSO-d6) δ [ppm]:
8.63 (d, J=1.6 Hz, 2H), 8.39 (d, J=8.0 Hz, 2H), 8.12 (d, J=8.0 Hz, 2H),
7.92 (dd, J=8.0, 1.6 Hz, 2H) 7.88 (s, 2H), 7.64-7.78 (m, 16H),
7.54-7.58 (m, 2H), 7.30-7.48 (m, 12H).

Working Example 2

Synthesis of Fluorine Atom-Containing Compound B

Working Example 2-1

Synthesis of Intermediate D

[Chem. 35]

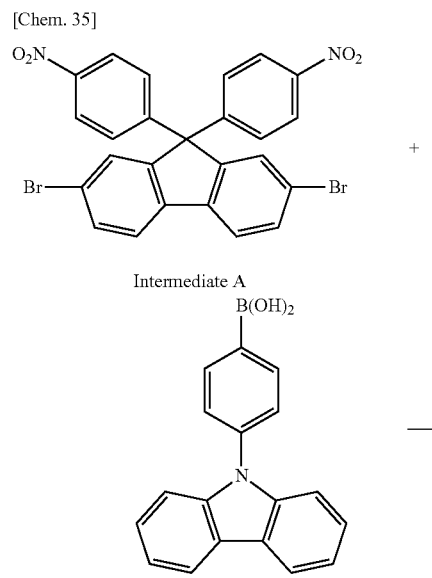

Intermediate A

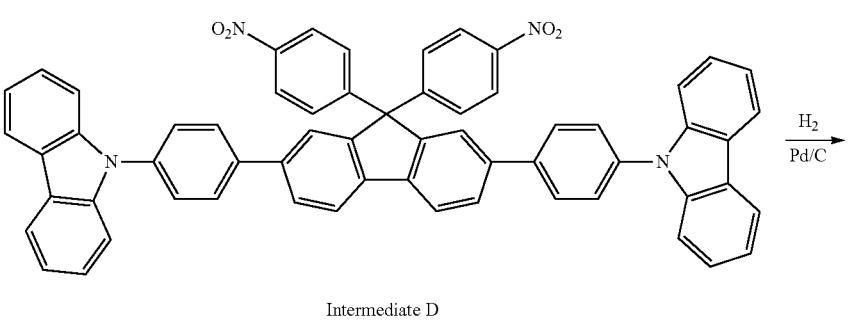

Intermediate D

A reactor was charged with 1.81 g of Intermediate A, 2.28 g of (4-(9H-carbazol-9-yl)phenyl)boronic acid, 0.18 g of tetrakistriphenylphosphine palladium, 0.30 g of trioctylmethylammonium chloride (Aliquat 336), 18 mL of tetrahydrofuran and 12 mL of a 2 mol/L aqueous solution of potassium carbonate. The reactor was flushed with nitrogen, after which the reactor contents were stirred for 3 hours at 60° C. The reaction mixture was returned to room temperature, following which toluene was added and liquid separation was carried out. The solvent in the resulting organic layer was driven off under reduced pressure. A mixed solvent of chloroform and n-hexane was added to the concentration residue, and the system was left to stand awhile at room temperature, following which the resulting suspension was filtered. The filtered matter was dried, giving 2.46 g (yield, 87%) of the target substance Intermediate D (9,9'-((9,9-bis(4-nitrophenyl)-9H-fluoren-2,7-diyl)bis(4,1-phenylene)) bis(9H-carbazole)). The $^1$H-NMR measurement results are shown below.

$^1$H-NMR (400 MHz, THF-d8) δ [ppm]:
8.19 (d, J=9.2 Hz, 4H), 8.11-8.15 (m, 6H), 7.90-7.95 (m, 8H),
7.68 (d, J=8.8 Hz, 4H), 7.64 (d, J=9.2 Hz, 4H), 7.34-7.42 (m, 8H),
7.21-7.25 (m, 4H).

Working Example 2-2

Synthesis of Intermediate E

[Chem. 36]

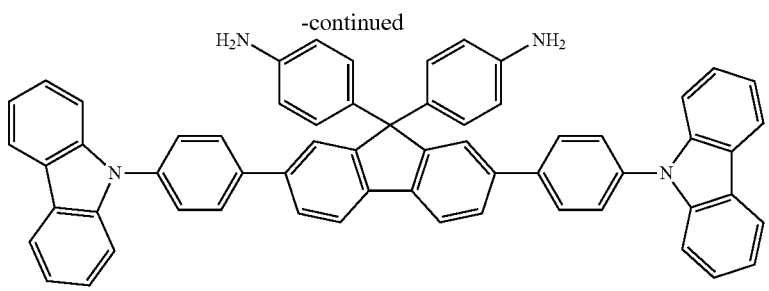

Intermediate E

A reactor was charged with 1.80 g of Intermediate D, 0.31 g of 5% palladium on carbon (AER type, from N.E. Chemcat Corporation; containing 49% water) and 18 mL of tetrahydrofuran. The reactor was flushed with nitrogen, after which the reactor contents were stirred for 53 hours at 50° C. The reaction mixture was returned to room temperature, following which tetrahydrofuran was added and filtration was carried out. The filtrate was concentrated, the concentrate was added dropwise to n-hexane, and the suspension was stirred at room temperature, following which filtration was carried out. The filtered matter was dried, giving 1.28 g of a mixture containing the target substance Intermediate E (4,4'-(2,7-bis(4-(9H-carbazol-9-yl)phenyl)-9H-fluoren-9,9-diyl)dianiline). Further purification was not carried out, and this mixture was used as the feedstock for the next step.

Working Example 2-3

Synthesis of Fluorine Atom-Containing Compound B

[Chem. 37]

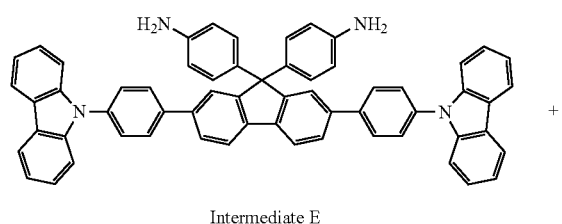

Intermediate E

+

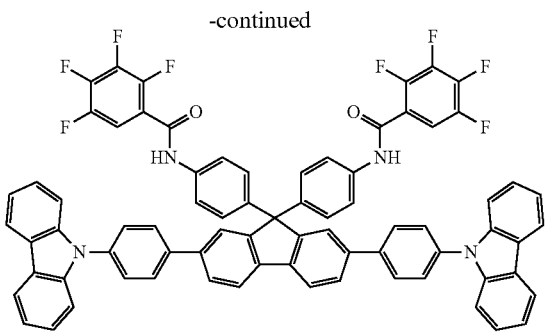

Fluorine Atom-Containing Compound B

A reactor was charged with 1.00 g of the above Intermediate E-containing mixture, 10 mL of N,N-dimethylformamide and 450 μL of trimethylamine. The reactor was flushed with nitrogen, after which 0.62 g of 2,3,4,5-tetrafluorobenzoyl chloride was added dropwise under cooling in an ice bath. Following the completion of dropwise addition, the system was stirred at room temperature for 0.5 hour. The reaction mixture was added dropwise to deionized water, following which the system was stirred in this state for 0.5 hour at room temperature. The resulting suspension was filtered, following which the filtered matter was dissolved in chloroform and added dropwise to n-hexane, and the resulting suspension was stirred at room temperature. Filtration was then carried out and the filtered matter thus obtained was purified by column chromatography. The fractions containing the target substance were collected and the solvent was driven off under reduced pressure. The concentration residue was dissolved in chloroform, the resulting solution was added dropwise to methanol, and the suspension was stirred for 0.5 hour at room temperature. Filtration was carried out and the filtered matter was dried, giving 0.88 g (yield, 62%) of the target substance Fluorine Atom-Containing Compound B (N,N'-((2,7-bis(4-(9H-carbazol-9-yl)phenyl)-9H-fluoren-9,9-diyl)bis(4,1-phenylene)) bis(2,3,4,5-tetrafluorobenzamide)). The $^1$H-NMR measurement results are shown below.

$^1$H-NMR (400 MHz, DMSO-d6) δ [ppm]:
10.63 (s, 2H), 8.23 (d, J=8.0 Hz, 4H), 8.15 (d, J=8.0 Hz, 2H),
7.96 (d, J=8.8 Hz, 4H) 7.87-7.90 (m, 4H), 7.69 (d, J=8.8 Hz, 6H),
7.64 (d, J=8.8 Hz, 4H), 7.39-7.44 (m, 8H), 7.33 (d, J=8.8 Hz, 4H),
7.25-7.29 (m, 4H).

Working Example 3

Synthesis of Fluorine Atom-Containing Compound C

Working Example 3-1

Synthesis of Intermediate F

[Chem. 38]

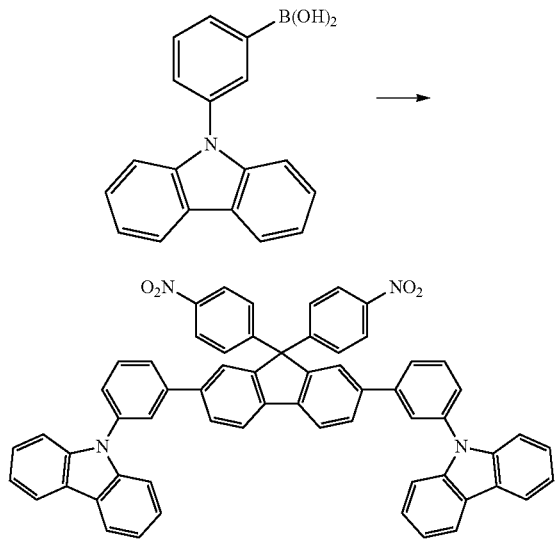

Intermediate F

A reactor was charged with 1.81 g of Intermediate A, 2.28 g of (3-(9H-carbazol-9-yl)phenyl)boronic acid, 0.18 g of tetrakistriphenylphosphine palladium, 0.32 g of trioctylmethylammonium chloride (Aliquat 336), 18 mL of tetrahydrofuran and 12 mL of a 2 mol/L aqueous solution of potassium carbonate. The reactor was flushed with nitrogen, after which the reactor contents were stirred for 3 hours at 60° C. The reaction mixture was returned to room temperature, following which toluene was added and liquid separation was carried out. The solvent in the resulting organic layer was driven off under reduced pressure. The concentration residue was purified by column chromatography (chloroform/n-hexane, 70/30→95/5), the fractions containing the target substance were collected, and the solvent was driven off under reduced pressure. The concentration residue was dissolved in chloroform and then added dropwise to n-hexane, following which the resulting suspension was filtered. The filtered matter was dried, giving 2.28 g (yield, 80%) of the target substance Intermediate F (9,9'-((9,9-bis(4-nitrophenyl)-9H-fluoren-2,7-diyl)bis(3,1-phenylene)) bis(9H-carbazole)). The $^1$H-NMR measurement results are shown below.

$^1$H-NMR (400 MHz, DMSO-d6) δ [ppm]:

8.26 (d, J=8.0 Hz, 4H), 8.18 (d, J=8.4 Hz, 2H), 8.14 (d, J=8.8 Hz, 4H), 7.94-7.96 (m, 6H), 7.85 (d, J=8.4 Hz, 2H), 7.76 (t, J=8.0 Hz, 2H), 7.61-7.63 (m, 2H), 7.57 (d, J=8.8 Hz, 4H), 7.41-7.44 (m, 8H), 7.28-7.32 (m, 4H).

Working Example 3-2

Synthesis of Intermediate G

[Chem. 39]

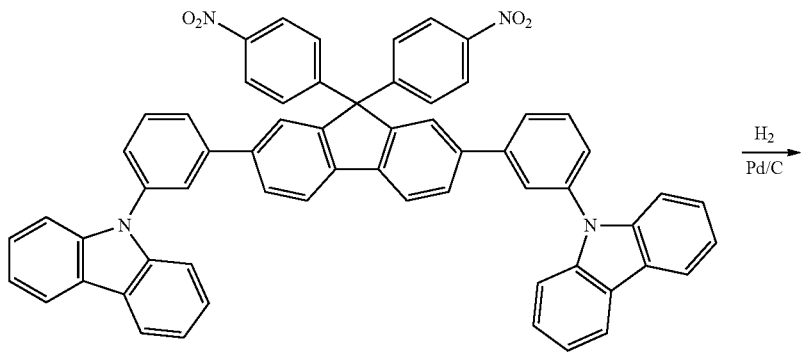

Intermediate F

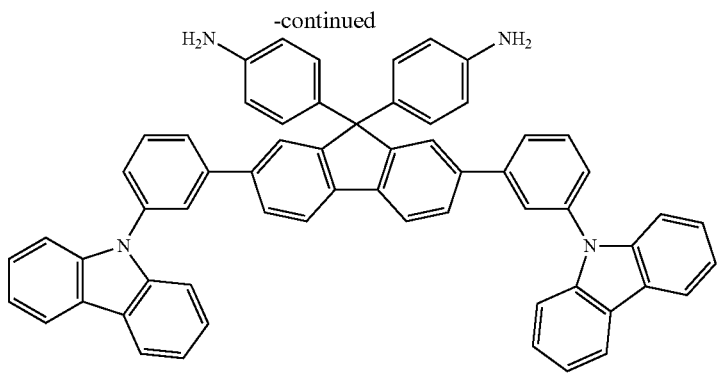

Intermediate G

A reactor was charged with 1.81 g of Intermediate F, 0.18 g of 5% palladium on carbon (AER type, from N.E. Chemcat Corporation; containing 49% water) and 18 mL of tetrahydrofuran. The reactor was flushed with nitrogen, after which the reactor contents were stirred for 33 hours at 50° C. The reaction mixture was returned to room temperature, following which tetrahydrofuran was added and filtration was carried out. The filtrate was concentrated, the concentrate was added dropwise to n-hexane, and the resulting suspension was stirred at room temperature, following which filtration was carried out. The filtered matter was dried, giving 1.56 g of a mixture containing Intermediate G (4,4'-(2,7-bis(3-(9H-carbazol-9-yl)phenyl)-9H-fluoren-9,9-diyl)dianiline). Further purification was not carried out, and this mixture was used as the feedstock for the next step.

Working Example 3-3

Synthesis of Fluorine Atom-Containing Compound C

[Chem. 40]

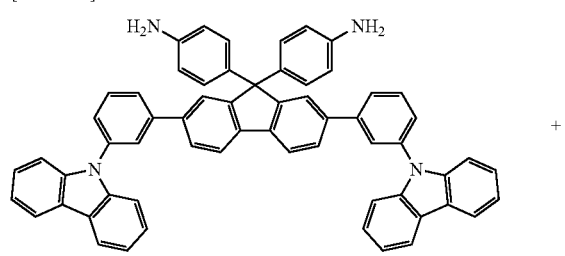

Intermediate G

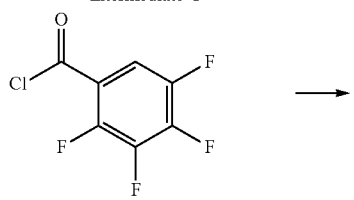

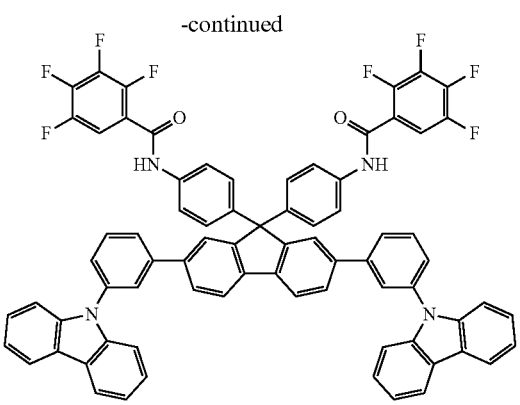

Fluorine Atom-Containing Compound C

A reactor was charged with 1.00 g of the above Intermediate G-containing mixture, 10 mL of N,N-dimethylformamide and 450 μL of trimethylamine. The reactor was flushed with nitrogen, after which 0.62 g of 2,3,4,5-tetrafluorobenzoyl chloride was added dropwise under cooling in an ice bath. Following the completion of dropwise addition, the system was stirred at room temperature for 2.5 hours. The reaction mixture was added dropwise to deionized water, following which the system was stirred in this state for 0.5 hour at room temperature. The resulting suspension was filtered, following which the filtered matter was dissolved in chloroform and added dropwise to methanol, and the resulting suspension was stirred at room temperature. Filtration was carried out and the resulting filtered matter was dried, giving 1.18 g (yield, 83%) of the target substance Fluorine Atom-Containing Compound C (N,N'-((2,7-bis(3-(9H-carbazol-9-yl)phenyl)-9H-fluoren-9,9-diyl)bis(4,1-phenylene))bis(2,3,4,5-tetrafluorobenzamide)). The $^1$H-NMR measurement results are shown below.

$^1$H-NMR (400 MHz, DMSO-d6) δ[ppm]:
10.59 (s, 2H), 8.26 (d, J=7.6 Hz, 4H), 8.11 (d, J=8.4 Hz, 2H), 7.82-7.93 (m, 8H),
7.76 (t, J=7.6 Hz, 2H), 7.66-7.73 (m, 2H), 7.59-7.63 (m, 6H), 7.42-7.47 (m, 8H),
7.26-7.33 (m, 8H).

Working Example 4

Synthesis of Fluorine Atom-Containing Compound D

Working Example 4-1

Synthesis of Intermediate H

[Chem. 41]

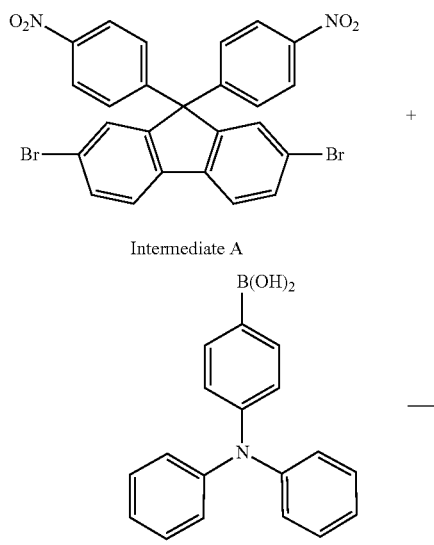

Intermediate A

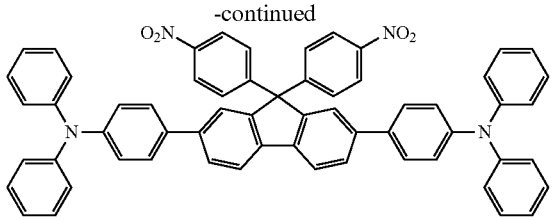

Intermediate H

A reactor was charged with 1.80 g of Intermediate A, 2.30 g of (4-diphenylamino)phenylboronic acid, 0.18 g of tetrakistriphenylphosphine palladium, 0.28 g of trioctylmethylammonium chloride (Aliquat 336), 18 mL of tetrahydrofuran and 12 mL of a 2 mol/L aqueous solution of potassium carbonate. The reactor was flushed with nitrogen, after which the reactor contents were stirred for 4.5 hours at 60° C. The reaction mixture was returned to room temperature, following which toluene and saturated saline water were added and liquid separation was carried out. The solvent in the resulting organic layer was driven off under reduced pressure, and the suspension was filtered. The filtered matter was dried, giving 2.39 g (yield, 84%) of the target substance Intermediate H (4,4'-((9,9-bis(4-nitrophenyl)-9H-fluoren-2,7-diyl)bis(N,N-diphenylaniline)). The $^1$H-NMR measurement results are shown below.

$^1$H-NMR (400 MHz, THF-d8) δ [ppm]:
8.11 (d, J=9.2 Hz, 4H), 7.95 (d, J=8.0 Hz, 2H), 7.69-7.73 (m, 4H),
7.54 (d, J=8.8 Hz, 4H), 7.47 (d, J=8.8 Hz, 4H), 7.20-7.25 (m, 8H),
7.04-7.07 (m, 12H), 6.99 (t, J=7.2 Hz, 4H).

Working Example 4-2

Synthesis of Intermediate I

[Chem. 42]

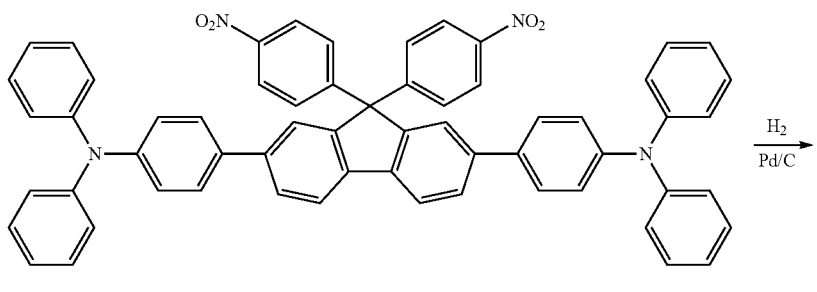

Intermediate H

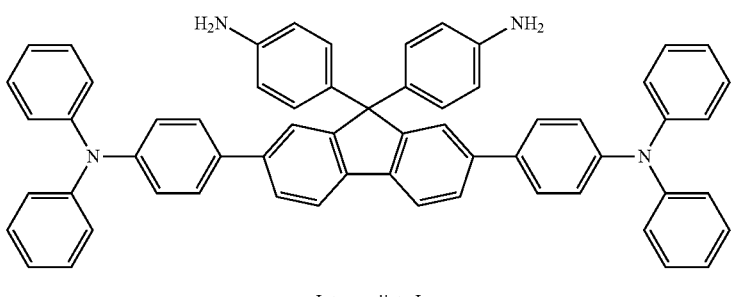

Intermediate I

A reactor was charged with 1.80 g of Intermediate H, 0.18 g of 5% palladium on carbon (AER type, from N.E. Chemcat Corporation; containing 49% water) and 18 mL of tetrahydrofuran. The reactor was flushed with nitrogen, after which the reactor contents were stirred for 22.5 hours at 60° C. The reaction mixture was returned to room temperature, following which tetrahydrofuran was added and filtration was carried out. The filtrate was concentrated, the concentrate was added dropwise to n-hexane, and the resulting suspension was stirred at room temperature, following which filtration was carried out. The filtered matter was dried, giving 1.62 g of a mixture containing Intermediate I (4,4'-(9,9-bis(4-aminophenyl)-9H-fluoren-2,7-diyl)bis(N,N-diphenylamine)). Further purification was not carried out, and this mixture was used as the feedstock for the next step.

Working Example 4-3

Synthesis of Fluorine Atom-Containing Compound D

[Chem. 43]

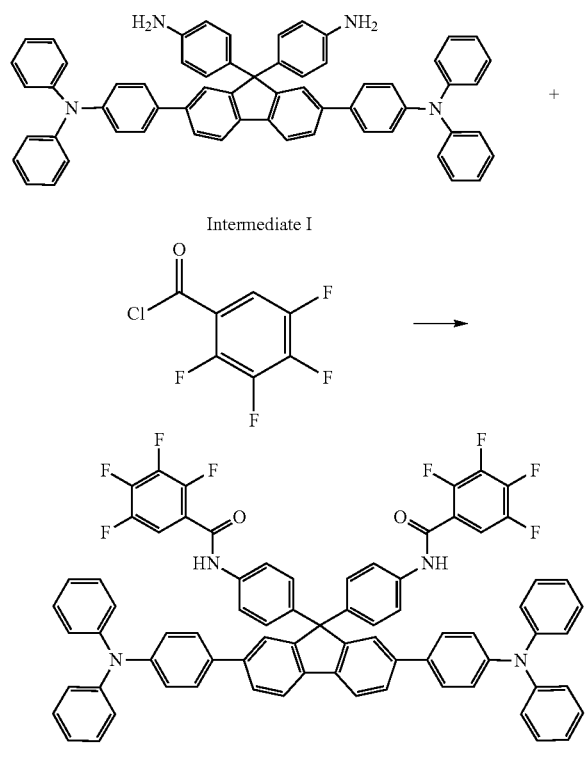

A reactor was charged with 0.50 g of the Intermediate I-containing mixture, 30 mL of N,N-dimethylformamide and 330 µL of trimethylamine. The reactor was flushed with nitrogen, after which 0.47 g of 2,3,4,5-tetrafluorobenzoyl chloride was added dropwise under cooling in an ice bath. Following the completion of dropwise addition, the system was stirred at room temperature for 2.5 hours. The reaction mixture was added dropwise to deionized water, following which the system was stirred in this state for 0.5 hour at room temperature. The resulting suspension was filtered, after which the filtered matter was dissolved in chloroform. Deionized water was added thereto and liquid separation was carried out. The organic phase was dried over anhydrous sodium sulfate, following which the solvent was driven off under reduced pressure. The concentration was added dropwise to a mixed solvent of methanol and n-hexane, and the resulting suspension was stirred at room temperature. Filtration was carried out and the filtered matter was dried, giving 0.45 g (yield, 63%) of the target substance Fluorine Atom-Containing Compound D (N,N'-((2,7-bis(4-(diphenylamino)phenyl)-9H-fluoren-9,9-diyl)bis(4,1-phenylene)) bis(2,3,4,5-tetrafluorobenzamide)). The $^1$H-NMR measurement results are shown below.

$^1$H-NMR (400 MHz, DMSO-d6) δ [ppm]:
10.59 (s, 2H), 7.98 (d, J=8.0 Hz, 2H), 7.64-7.70 (m, 6H), 7.55-7.58 (m, 8H),
7.25-7.29 (m, 8H), 7.21 (d, J=8.8 Hz, 4H), 6.98-7.04 (m, 16H).

[2] Preparation of Charge-Transporting Varnishes

Working Example 5

Preparation of Charge-Transporting Varnish A

Charge-Transporting Varnish A was obtained by dissolving 150 mg of Fluorine Atom-Containing Compound A in 5 g of N,N-dimethylisobutyramide (DMIB), stirring and then filtering the resulting solution using a polytetrafluoroethylene (PTFE) filter having a pore size of 0.2 µm.

Working Example 6

Preparation of Charge-Transporting Varnish B

Charge-Transporting Varnish B was obtained by dissolving 150 mg of Fluorine Atom-Containing Compound B in 5 g of DMIB, stirring and then filtering the resulting solution using a PTFE filter having a pore size of 0.2 µm.

Working Example 7

Preparation of Charge-Transporting Varnish C

Charge-Transporting Varnish C was obtained by dissolving 100 mg of Fluorine Atom-Containing Compound C in a mixed solvent of 1.65 g of 1,3-dimethyl-2-imidazolidinone (DMI), 2 g of 2,3-butanediol (2,3-BD) and 1.35 g of dipropylene glycol monomethyl ether (DPM), stirring and then filtering the resulting solution using a PTFE filter having a pore size of 0.2 µm.

Working Example 8

Preparation of Charge-Transporting Varnish D

Charge-Transporting Varnish D was obtained by dissolving 100 mg of Fluorine Atom-Containing Compound D in a mixed solvent of 1.65 g of DMI, 2 g of 2,3-BD and 1.35 g of DPM, stirring and then filtering the resulting solution using a PTFE filter having a pore size of 0.2 µm.

Comparative Example 1

Preparation of Charge-Transporting Varnish E

Charge-Transporting Varnish E was obtained by dissolving 50 mg of TFB Polymer (LT-N148, from Luminescence Technology) of the following formula in a mixed solvent of 2.5 g of 3-phenoxytoluene and 2.5 g of cyclohexylbenzene, stirring and then filtering the resulting solution using a PTFE filter having a pore size of 0.2 µm.

[Chem. 44]

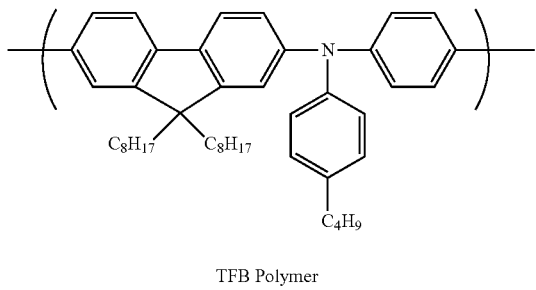

TFB Polymer

[3] Device Fabrication and Evaluation of Device Characteristics

In the following Working Examples and Comparative Examples, a glass substrate with dimensions of 25 mm×25 mm×0.7 mm (t) and having ITO patterned on the surface to a film thickness of 150 nm was used as an ITO substrate. Prior to use, impurities on the surface were removed with an 02 plasma cleaning system (150 W, 30 seconds).

[3-1] Fabrication of Hole-Only Devices (HOD) and Evaluation of Device Characteristics Working Example 9

Charge-Transporting Varnish A was coated onto an ITO substrate using a spin coater and was subsequently, in open air, pre-baked at 80° C. for 1 minute and then subjected to a main bake at 230° C. for 15 minutes, thereby forming a 30 nm thin film on the ITO substrate.

Next, using a vapor deposition system (degree of vacuum, $2.0 \times 10^{-5}$ Pa), a thin film of aluminum was deposited thereon, giving a HOD. Vapor deposition was carried out at a deposition rate of 0.2 nm/s. The thickness of the aluminum thin film was set to 80 nm.

To prevent the device characteristics from deteriorating due to the influence of oxygen, moisture and the like in air, the HOD was sealed with sealing substrates, following which the characteristics were evaluated. Sealing was carried out by the following procedure.

The HOD was placed between sealing substrates in a nitrogen atmosphere having an oxygen concentration of 2 ppm or less and a dew point of not more than −85° C., and the sealing substrates were laminated together using an adhesive (MORESCO Moisture Cut WB90US(P), from Moresco Corporation). At this time, a desiccant (HD-071010W-40, from Dynic Corporation) was placed, together with the HOD, within the sealing substrates. The laminated sealing substrates were irradiated with UV light (wavelength, 365 nm; dosage, 6,000 mJ/cm$^2$) and then annealed at 80° C. for 1 hour to cure the adhesive.

Working Examples 10 to 12

Aside from using Charge-Transporting Varnishes B to D instead of Charge-Transporting Varnish A, HODs were fabricated in the same way as in Working Example 9.

Comparative Example 2

Aside from using Charge-Transporting Varnish E instead of Charge-Transporting Varnish A, an HOD was fabricated in the same way as in Working Example 9.

[3-2] Fabrication of Electron-Only Devices (EOD) and Evaluation of Device Characteristics Working Example 13

A glass substrate with dimensions of 25 mm×25 mm×0.7 mm (t) and having Al/Nd patterned on the surface to a film thickness of 150 nm was used as an Al/Nd substrate. Prior to use, impurities on the surface were removed with an O$_2$ plasma cleaning system (150 W, 30 seconds). Next, Charge-Transporting Varnish A was coated onto the Al/Nd substrate using a spin coater and was subsequently, in open air, pre-baked at 80° C. for 1 minute and then subjected to a main bake at 230° C. for 15 minutes, thereby forming a 30 nm thin film on the Al/Nd substrate.

Next, using a vapor deposition system (degree of vacuum, $2.0 \times 10^{-5}$ Pa), a thin film of aluminum was deposited thereon, giving an EOD. Vapor deposition was carried out at a deposition rate of 0.2 nm/s. The thickness of the aluminum thin film was set to 80 nm.

To prevent the device characteristics from deteriorating due to the influence of oxygen, moisture and the like in air, the EOD was sealed with sealing substrates, following which the characteristics were evaluated. Sealing was carried out in the same way as described above.

Working Examples 14 to 16

Aside from using Charge-Transporting Varnishes B to D instead of Charge-Transporting Varnish A, EODs were fabricated in the same way as in Working Example 13.

Comparative Example 3

Aside from using Charge-Transporting Varnish E instead of Charge-Transporting Varnish A, an EOD was fabricated in the same way as in Working Example 13.

The current densities at a driving voltage of 3 V were measured for the HODs and EODs fabricated in the above Working Examples and Comparative Examples. The results are shown in Table 7.

TABLE 7

| | Charge-transporting varnish | Current density (mA/cm$^2$) | |
|---|---|---|---|
| | | HOD | EOD |
| Working Examples 9, 13 | A | $1.84 \times 10^2$ | $5.67 \times 10^{-5}$ |
| Working Examples 10, 14 | B | $1.92 \times 10^2$ | $6.94 \times 10^{-3}$ |
| Working Examples 11, 15 | C | $1.06 \times 10^2$ | $5.48 \times 10^{-5}$ |
| Working Examples 12, 16 | D | $1.37 \times 10^2$ | $1.09 \times 10^{-5}$ |
| Comparative Examples 2, 3 | E | $9.13 \times 10^1$ | $6.81 \times 10^{-1}$ |

As shown in Table 7, the compounds in the Working Examples prepared from the charge transporting varnishes of the invention exhibited a greater hole transportability than the TFB polymer in the Comparative Examples, and moreover had a better electron-blocking ability than the TFB polymer in the Comparative Examples.

The invention claimed is:

1. A fluorine atom-containing compound of formula (1) below

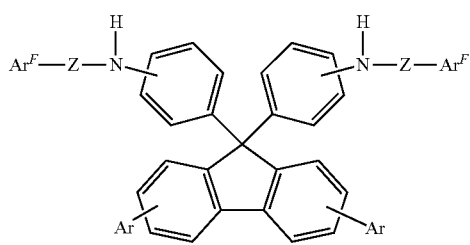
(1)

wherein Z is a group of any of formulas (2) to (7) below

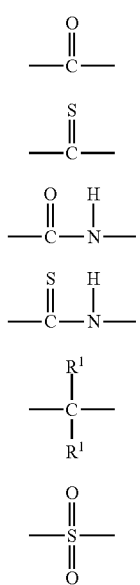

(2)
(3)
(4)
(5)
(6)
(7)

each $R^1$ is independently a hydrogen atom or an alkyl group of 1 to 20 carbon atoms;

each Ar is independently a group of any of formulas (8) to (11) below

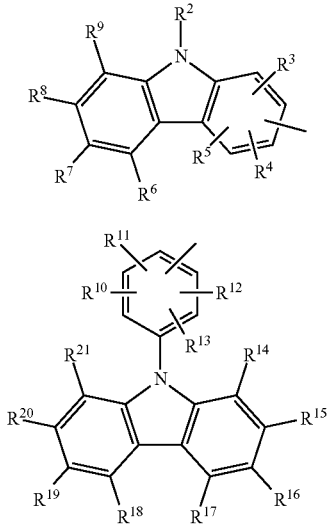

(8)
(9)

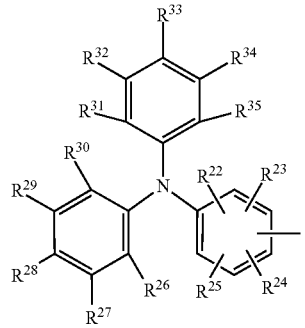
(10)

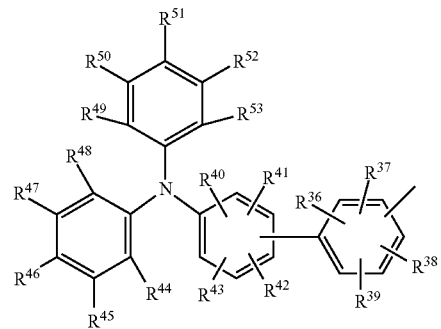
(11)

$R^2$ in formula (8) is a hydrogen atom, an alkyl group of 1 to 20 carbon atoms, an aryl group of 6 to 20 carbon atoms which may be substituted with a cyano group, a nitro group, a halogen atom, an alkyl group of 1 to 20 carbon atoms or a haloalkyl group of 1 to 20 carbon atoms, or a group of any of formulas (12) to (14) below

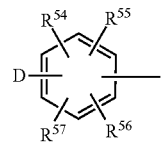
(12)

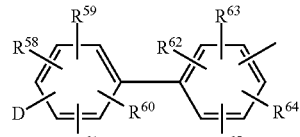
(13)

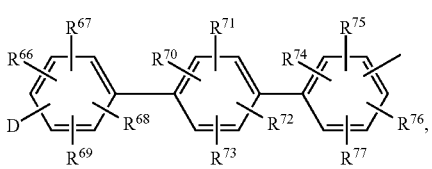
(14)

wherein D is a diarylamino group in which the aryl groups are each independently an aryl group of 6 to 20 carbon atoms; and $R^3$ to $R^{77}$ in formulas (8) to (14) are each independently a hydrogen atom, a cyano group, a nitro group, a halogen atom, an alkyl group of 1 to 20 carbon atoms or a haloalkyl group of 1 to 20 carbon atoms; and each $Ar^F$ is independently a fluoroaryl group of 6 to 20 carbon atoms which may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms; an aryl group of 6 to 20 carbon atoms which, along with being substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, may also be substituted with a cyano group, a halogen atom or a fluoroalkoxy group of 1 to 20 carbon atoms; a phenyl group substituted with 1 to 3 trifluoromethyl groups; or a 4-ethoxy-3-(trifluoromethyl)phenyl group.

2. The fluorine atom-containing compound of claim 1, wherein each Ar$^F$ is independently a phenyl group substituted with 3 or more fluorine atoms which may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms; or a 2-(trifluoromethyl)phenyl group, 3-(trifluoromethyl)phenyl group, 4-(trifluoromethyl)phenyl group, 4-ethoxy-3-(trifluoromethyl)phenyl group, 3-fluoro-4-(trifluoromethyl)phenyl group, 4-fluoro-3-(trifluoromethyl)phenyl group, 4-fluoro-2-(trifluoromethyl)phenyl group, 2-fluoro-5-(trifluoromethyl)phenyl group, 3-fluoro-5-(trifluoromethyl)phenyl group, 3,5-di(trifluoromethyl)phenyl group, 2,4,6-tri(trifluoromethyl)phenyl group, 4-(pentafluoroethyl)phenyl group, 4-(3,3,3-trifluoropropyl)phenyl group, 2,3,5,6-tetrafluoro-4-(trifluoromethyl)phenyl group, 4-(perfluorovinyl)phenyl group, 4-(perfluoropropenyl)phenyl group or 4-(perfluorobutenyl)phenyl group.

3. The fluorine atom-containing compound of claim 1 or 2, wherein the Ar$^F$ groups are identical groups.

4. The fluorine atom-containing compound of claim 1, wherein Z is a group of formula (2).

5. The fluorine atom-containing compound of claim 1, wherein R$^2$ is a phenyl group.

6. The fluorine atom-containing compound of claim 1, wherein R$^3$ to R$^{77}$ are hydrogen atoms.

7. A charge-transporting substance comprising the fluorine atom-containing compound of claim 1.

8. A charge-transporting varnish comprising the charge-transporting substance of claim 7 and an organic solvent.

9. The charge-transporting varnish of claim 8, further comprising a charge-transporting substance that is free of fluorine atoms.

10. The charge-transporting varnish of claim 8 or 9, further comprising a dopant.

11. A charge-transporting thin film produced using the charge-transporting varnish of claim 8.

12. An organic electroluminescent device comprising the charge-transporting thin film of claim 11.

13. A method of producing a fluorine atom-containing compound of formula (1) below, which method comprises the steps of:

reacting a compound of formula (15) with a compound of formula (16) to obtain an intermediate of formula (17);

reducing the intermediate of formula (17) to obtain an intermediate of formula (18); and reacting the intermediate of formula (18) with a compound of formula (19)

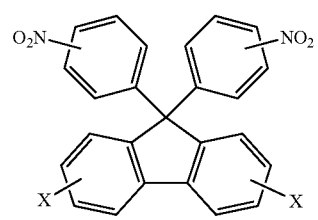

(15)

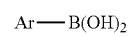

(16)

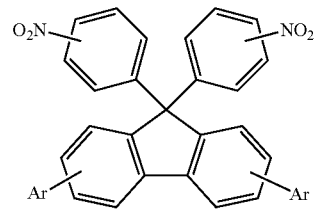

(17)

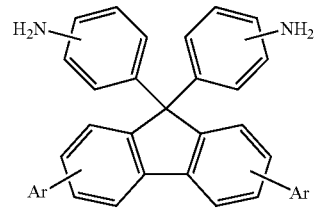

(18)

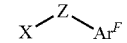

(19)

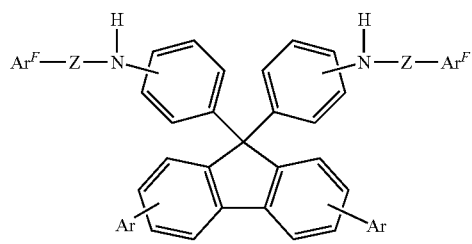

(1)

wherein Z is a group of any of formulas (2) to (7) below

(2)

(3)

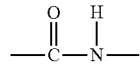

(4)

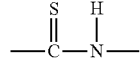

(5)

(6)

-continued

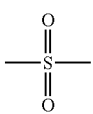
(7)

each $R^1$ is independently a hydrogen atom or an alkyl group of 1 to 20 carbon atoms;

each Ar is independently a group of any of formulas (8) to (11) below

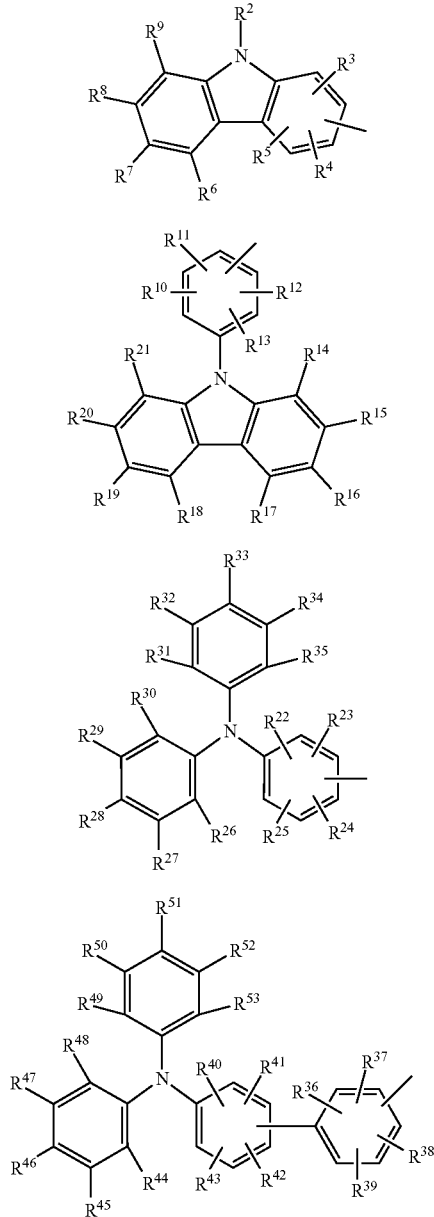

$R^2$ is a hydrogen atom, an alkyl group of 1 to 20 carbon atoms, an aryl group of 6 to 20 carbon atoms which may be substituted with a cyano group, a nitro group, a halogen atom, an alkyl group of 1 to 20 carbon atoms or a haloalkyl group of 1 to 20 carbon atoms, or a group of any of formulas (12) to (14) below

(12)

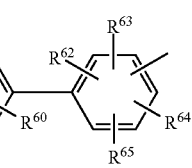
(13)

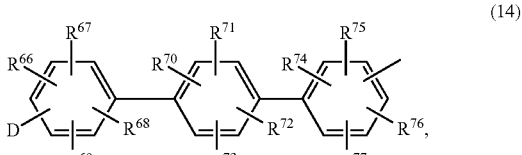
(14)

wherein D is a diarylamino group in which the aryl groups are each independently an aryl group of 6 to 20 carbon atoms; and $R^3$ to $R^{77}$ in formulas (8) to (14) is each independently a hydrogen atom, a cyano group, a nitro group, a halogen atom, an alkyl group of 1 to 20 carbon atoms or a haloalkyl group of 1 to 20 carbon atoms;

each $Ar^F$ is independently a fluoroaryl group of 6 to 20 carbon atoms which may be substituted with a cyano group, a chlorine atom, a bromine atom, an iodine atom, a nitro group, an alkyl group of 1 to 20 carbon atoms, a fluoroalkyl group of 1 to 20 carbon atoms or a fluoroalkoxy group of 1 to 20 carbon atoms; or an aryl group of 6 to 20 carbon atoms which, along with being substituted with a fluoroalkyl group of 1 to 20 carbon atoms, a fluorocycloalkyl group of 3 to 20 carbon atoms, a fluorobicycloalkyl group of 4 to 20 carbon atoms, a fluoroalkenyl group of 2 to 20 carbon atoms or a fluoroalkynyl group of 2 to 20 carbon atoms, may also be substituted with a cyano group, a halogen atom or a fluoroalkoxy group of 1 to 20 carbon atoms; and X is a halogen atom methanesulfonyloxy group, fluoroalkylsulfonyloxy group, or aromatic sulfonyloxy group.

* * * * *